(12) United States Patent
Ostroff et al.

(10) Patent No.: US 10,532,208 B2
(45) Date of Patent: *Jan. 14, 2020

(54) MINIATURE IMPLANTABLE NEUROSTIMULATOR SYSTEM FOR SCIATIC NERVES AND THEIR BRANCHES

(71) Applicant: Nine Continents Medical, Inc., Livermore, CA (US)

(72) Inventors: Alan Ostroff, Pleasanton, CA (US); Peter Jacobson, Livermore, CA (US)

(73) Assignee: Nine Continents Medical, Inc., Livermore, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/222,246

(22) Filed: Dec. 17, 2018

(65) Prior Publication Data
US 2019/0184161 A1    Jun. 20, 2019

Related U.S. Application Data

(63) Continuation of application No. 15/880,373, filed on Jan. 25, 2018, now Pat. No. 10,195,425, which is a
(Continued)

(51) Int. Cl.
*A61N 1/00* (2006.01)
*A61N 1/36* (2006.01)
(Continued)

(52) U.S. Cl.
CPC ....... *A61N 1/36007* (2013.01); *A61N 1/0556* (2013.01); *A61N 1/0558* (2013.01); *A61N 1/3606* (2013.01); *A61N 1/36057* (2013.01); *A61N 1/36125* (2013.01); *A61N 1/36171* (2013.01); *A61N 1/36175* (2013.01);
(Continued)

(58) Field of Classification Search
CPC .............. A61N 1/36007; A61N 1/0556; A61N 1/0558; A61N 1/3606; A61N 1/36171; A61N 1/36175; A61N 1/3787; A61N 1/37205; A61N 1/37223; A61N 1/37235
See application file for complete search history.

(56) References Cited

U.S. PATENT DOCUMENTS 5,327,909 A    7/1994 Kiser et al.
6,409,674 B1    6/2002 Brockway et al.
(Continued)

FOREIGN PATENT DOCUMENTS

WO    WO-2009080785 A1    7/2009

OTHER PUBLICATIONS

"EP15833299.9 European Search Report dated Feb. 23, 2018".
(Continued)

*Primary Examiner* — Mallika D Fairchild
(74) *Attorney, Agent, or Firm* — Wilson Sonsini Goodrich and Rosati, P.C.

(57) ABSTRACT

This application describes a miniature implantable neurostimulator system for sciatic nerves and their branches. The implanted miniature neurostimulator is implanted in the leg and stimulates these nerves for the treatment of urinary or bowel incontinence. The miniature implantable neurostimulator has a low duty cycle permitting a small size with medically-acceptable longevity. The system includes a wireless programmer and patient-activated key fob.

32 Claims, 21 Drawing Sheets

Related U.S. Application Data continuation of application No. 15/424,683, filed on Feb. 3, 2017, now Pat. No. 9,913,980, which is a continuation of application No. PCT/US2015/045138, filed on Aug. 13, 2015.

(60) Provisional application No. 62/038,308, filed on Aug. 17, 2014, provisional application No. 62/038,316, filed on Aug. 17, 2014, provisional application No. 62/102,543, filed on Jan. 12, 2015.

(51) Int. Cl.
*A61N 1/375* (2006.01)
*A61N 1/378* (2006.01)
*A61N 1/05* (2006.01)
*A61N 1/372* (2006.01)

(52) U.S. Cl.
CPC ......... *A61N 1/3756* (2013.01); *A61N 1/3787* (2013.01); *A61N 1/37205* (2013.01); *A61N 1/37223* (2013.01); *A61N 1/37235* (2013.01); *A61N 1/3758* (2013.01); *A61N 1/37252* (2013.01)

(56) References Cited

U.S. PATENT DOCUMENTS

| | | | |
|---|---|---|---|
| 9,913,980 B2 | 3/2018 | Ostroff et al. | |
| 10,195,425 B2 | 2/2019 | Ostroff et al. | |
| 2002/0055761 A1 | 5/2002 | Mann et al. | |
| 2002/0123780 A1 | 9/2002 | Grill et al. | |
| 2003/0114905 A1 | 6/2003 | Kuzma | |
| 2006/0149345 A1 | 7/2006 | Boggs et al. | |
| 2006/0155345 A1 | 7/2006 | Williams et al. | |
| 2007/0060980 A1 | 3/2007 | Strother et al. | |
| 2007/0100408 A1 | 5/2007 | Gerber | |
| 2008/0039915 A1 | 2/2008 | Van Den Biggelaar et al. | |
| 2008/0221383 A1 | 9/2008 | Way et al. | |
| 2009/0210019 A1 | 8/2009 | Kim et al. | |
| 2010/0176808 A1 | 7/2010 | Legay | |
| 2010/0304209 A1 | 12/2010 | Lund et al. | |
| 2011/0004269 A1 | 1/2011 | Strother et al. | |
| 2013/0310706 A1 | 11/2013 | Stone et al. | |
| 2014/0058476 A1 | 2/2014 | Crosby et al. | |
| 2014/0214125 A1 | 7/2014 | Greiner et al. | |
| 2014/0379048 A1 | 12/2014 | Von Arx et al. | |
| 2015/0173655 A1 | 6/2015 | Demmer et al. | |

OTHER PUBLICATIONS

International Search Report dated Jan. 7, 2016 for International PCT Application No. PCT/US2015/045138.
Notice of Allowance dated Nov. 30, 2017 for U.S. Appl. No. 15/424,683.
Office Action dated Oct. 2, 2017 for U.S. Appl. No. 15/424,683.
U.S. Appl. No. 15/424,683 Notice of Allowance dated Jan. 25, 2018.
U.S. Appl. No. 15/880,373 Office Action dated May 2, 2018.

MINIATURE IMPLANTABLE NEUROSTIMULATOR SYSTEM FOR SCIATIC NERVES AND THEIR BRANCHES

CROSS-REFERENCE

This application is a continuation of U.S. patent application Ser. No. 15/880,373, filed Jan. 25, 2018, now U.S. Pat. No. 10,195,425 issued on Feb. 5, 2019, which is a continuation of U.S. patent application Ser. No. 15/424,683, filed Feb. 3, 2017, now U.S. Pat. No. 9,913,980 issued on Mar. 13, 2018, which is a continuation of PCT Application No. PCT/US15/45138, filed Aug. 13, 2015, which claims the benefit of U.S. Provisional Applications No. 62/038,308, filed Aug. 17, 2014, 62/038,316, filed Aug. 17, 2014, and 62/102,543, filed Jan. 12, 2015, which applications are incorporated herein by reference.

BACKGROUND

The present disclosure relates to medical devices, systems, and methods. In particular, the present disclosure relates to medical devices, systems, and methods for stimulating tissue such as nerves to treat various indications. Indications of interest may include urinary and bowel incontinence, for example. Stimulation devices and therapies for urinary and bowel incontinence are currently available in the marketplace but may be limited in at least some cases.

A sacral nerve stimulator, InterStim II, marketed by Medtronic Inc., of Fridley, Minn., provides therapy for urinary or bowel incontinence through the use of electrical stimulation of the sacral nerve by a long-term active implantable device. The InterStim II implantable generator is large, at 14 cc, and must be implanted in the upper buttock. A long lead wire, 33 cm, must then be tunneled to the stimulation site. The generator typically lasts approximately 4.4 years due to the relatively high duty-cycle stimulation requirement of 16 seconds ON, 8 seconds OFF at an amplitude of 3 V, rate of 14 Hz and pulse width of 210 µs.

InterStim patients undergo an invasive qualification step before the generator is implanted, to verify that the therapy has a high likelihood of success. The qualification step requires the implantation of a temporary electrode connected to a transcutaneous wire that plugs into an external neurostimulator carried by the patient, typically for 3 to 5 days.

PTNS (Percutaneous Tibial Nerve Stimulation), marketed by Uroplasty, Inc, of Minnetonka, Minn., also provides therapy for urinary incontinence through electrical stimulation of the tibial nerve via a percutaneous needle electrode. Electrical stimulation is provided by an external stimulator programmed to delivery therapy for approximately 30 minutes. Initially patient sessions are typically scheduled once per week. Sessions can be scheduled less frequently once effective relief occurs.

Accordingly, there are needs for devices, systems, and methods for stimulation that address one or more of the above drawbacks such as large and uncomfortable implant size, low implant lifespan, invasive qualification steps, and too frequent patient sessions, to name a few.

SUMMARY

The present disclosure provides devices, systems, and methods for stimulating tissue. Disclosed is a miniature implantable neurostimulator for sciatic nerves and their branches providing therapy for urinary and bowel incontinence. The implanted neurostimulator is significantly smaller in volume than existing sacral neurostimulators while maintaining a medically-acceptable device longevity. By stimulating branches of the sciatic nerve and locating the miniature neurostimulator in the leg, the present disclosure provides an implantable alternative to sacral nerve stimulation, with a device that is potentially simpler to implant, safer, and more comfortable for patients.

Aspects of the present disclosure may provide methods for improving a urinary or bowel function in a subject. An incision may be created in a leg of a patient to access a stimulation site. An implant at or near the stimulation site may be placed through the incision. At least a portion of an electrode assembly of the implant may be positioned at or adjacent a sciatic nerve or a branch thereof in the stimulation site. The electrode assembly of the implant may direct a stimulation signal to the tissue of the subject. The stimulation signal may improve a urinary or bowel function in the subject, such as to treat urinary incontinence (e.g., overactive bladder (OAB) or bowel incontinence (BI). The stimulation signal may be directed with a low duty cycle of between 0.1% and 2.5%. The stimulation signal may be directed with a low current drain of a battery of the implant of between 0.1 µA to 5 µA. The low duty cycle and low current drain of the stimulation pulse may combine to provide a useful life of the implant in the body of at least 5 years without removal from the body.

The step of creating the incision in the leg may comprise a step of creating a tunnel in the leg for the implant. A first tunnel may be created from the incision into the tissue, and a second tunnel may be created from the incision into the tissue as well. To place the implant at or near the stimulation site, an enclosure of the implant may be placed into the first tunnel. To position the electrode assembly of the implant at or adjacent a sciatic nerve or a branch thereof, at least a portion of the electrode assembly may be positioned in the second tunnel. The first tunnel may be created in a first direction and the second tunnel may be created in a second direction opposite the first direction. The tunnel(s) in the leg is created with a blunt dissection tool. The blunt dissection tool may comprise an elongate rod with a ball nose at a first end and a handle on a second end opposite the first end. The elongate rod may be made of stainless steel and the handle may be made of a plastic or polymer. At least a portion of the blunt dissection tool may be radiopaque.

The step of creating the incision in the leg may comprise a step of creating a primary incision in the leg to access the stimulation site, creating a secondary incision in the leg, and creating a tunnel in the leg between the primary and secondary incisions. To place the implant in the stimulation site, the implant may be placed in the tunnel and the implant may be fixated in place through one or more of the primary or secondary incisions, such as by suturing. After the incision in the leg is made and the implant placed at or near the stimulation site, the incision may be closed.

Prior to placing the implant at or near the stimulation site or directing the stimulation signal to the tissue of the subject, the subject may be qualified for use of the implant. The subject may be qualified by applying a therapy from an external device to the subject to test the therapy with the subject. The qualifying therapy may be applied by percutaneously or transcutaneously stimulating the tissue with a signal generated from the external device, such as with its electrode array.

Not all OAB patients respond to neuromodulation. Consequently, users can choose to qualify patients before implanting a permanent pulse generator and lead. Percutaneous tibial nerve stimulation (PTNS), which may use a needle electrode and an external pulse generator, for example, during 12 weekly clinic visits, may be used to qualify patients. Alternatively or in combination, a percutaneous implantation of a temporary electrode-lead with no fixation feature may be performed and a wearable external pulse generator may be used for a trial period, for example, stimulating for 30 minutes each day for one or two weeks. The temporary electrode-lead can be removed without a surgical procedure. Alternatively or in combination, a permanent electrode-lead with a fixation feature may be implanted and a wearable external pulse generator may be used for a similar trial period. The use of the permanent lead can have a potential advantage of preventing false-negative qualifications due to electrode dislodgment or migration, but it may have a potential disadvantage of requiring responders and non-responders to undergo two surgical procedures. Alternatively, the permanent electrode-lead and pulse generator may be implanted without a previous qualification period ("straight to implant").

The useful life of the implant implanted in the body may be in a range between 5 and 35 years, 6 and 34 years, 7 and 33 years, 8 and 32 years, 9 and 31 years, 10 and 30 years, 11 and 29 years, 12 and 28 years, 13 and 27 years, 14 and 26 years, 15 and 25 years, 16 and 24 years, 17 and 23 years, 18 and 22 years, or 19 and 21 years. The background current drain may be in a range between 4.5 μA and 0.10 μA, 4.0 μA and 0.10 μA, 3.5 μA and 0.10 μA, 3.0 μA and 0.10 μA, 2.5 μA and 0.10 μA, 2.0 μA and 0.10 μA, 1.5 μA and 0.10 μA, 1.0 μA and 0.10 μA, 0.9 μA and 0.10 μA, 0.8 μA and 0.10 μA, 0.7 μA and 0.10 μA, 0.6 μA and 0.10 μA, 0.5 μA and 0.10 μA, 0.4 μA and 0.10 μA, 0.3 μA and 0.10 μA, or 0.2 μA and 0.1 μA.

The duty cycle of the stimulation signal may be in a range between 2.4% and 0.1%, 2.3% and 0.1%, 2.2% and 0.1%, 2.1% and 0.1%, 2.0% and 0.1%, 1.9% and 0.1%, 1.8% and 0.1%, 1.7% and 0.1%, 1.6% and 0.1%, 1.5% and 0.1%, 1.4% and 0.1%, 1.3% and 0.1%, 1.2% and 0.1%, 1.1% and 0.1%, 1.0% and 0.1%, 0.9% and 0.1%, 0.8% and 0.1%, 0.7% and 0.1%, 0.6% and 0.1%, 0.5% and 0.1%, 0.4% and 0.1%, 0.3% and 0.1%, or 0.2% and 0.1%. For example, the electrode assembly of the implant may direct the stimulation signal to the tissue of the subject for about 30 minutes once a week. In some cases, the electrode assembly of the implant may direct the stimulation signal to the tissue of the subject while the subject is asleep. Alternatively or in combination, the stimulation may be applied as the user, patient, or medical professional desires. PTNS applied once per week can take six weeks or more to show an effect. Patients who are desperate for an immediate cure could prefer more frequent stimulation at the start of therapy. Consequently, the implantable pulse generator of the implant can be configured to stimulate frequently just after implant to provide a faster response, and can then taper to less frequent stimulation afterwards to meet longevity objectives. This schedule can be preprogrammed or modified as necessary in real time, by the user, patient, or medical professional.

The stimulation signal may have a stimulation current in a range between 19 mA and 1 mA, 18 mA and 2 mA, 17 mA and 3 mA, 16 mA and 4 mA, 15 mA and 5 mA, 14 mA and 6 mA, 13 mA and 7 mA, 12 mA and 8 mA, or 11 mA and 9 mA. The generated stimulation signal may be charged balanced. The generated stimulation signal has a stimulation frequency or stimulation pulse rate in a range between 30 Hz and 10 Hz, 29 Hz and 11 Hz, 28 Hz and 12 Hz, 27 Hz and 13 Hz, 26 Hz and 14 Hz, 25 Hz and 15 Hz, 24 Hz and 16 Hz, 23 Hz and 17 Hz, 22 Hz and 18 Hz, or 21 Hz and 19 Hz. For example, the stimulation frequency may be from 20 Hz to 25 Hz, which a range shown to be effective to treat urinary and/or bowel incontinence with tibial nerve stimulation. The generated stimulation signal may have a stimulation pulse width in a range between 300 μs and 100 μs, 290 μs and 110 μs, 280 μs and 120 μs, 270 μs and 130 μs, 260 μs and 140 μs, 250 μs and 150 μs, 240 μs and 160 μs, 230 μs and 170 μs, 220 μs and 180 μs, or 210 μs and 190 μs. For example, a pulse pattern with 200 μs pulses at 20 Hz may be used because this pattern has been shown effective for to treat urinary and/or bowel incontinence with tibial nerve stimulation.

In other embodiments, different pulse patterns may be applied. For example, aspects of the present disclosure may encompass the treatment of other indications aside from urinary and/or bowel incontinence may be treated with different pulse patterns. Stimulation pulse patterns from 90 to 500 μs at 20 to 100 Hz may be applied and these patterns have been shown effective for relief from peripheral nerve pain. For peripheral nerve field stimulation, most patients prefer the frequency to be between 20 and 50 Hz. Anything higher than this range may be felt as a very strong sensation, or cause burning or pinching. Pulse width in the range of 90 to 250 μs may be best tolerated. Stimulation at higher frequencies, e.g. 1,200 Hz, have also been shown effective for relief from peripheral nerve pain and may have an additional advantage of not provoking a sensory response in the patient. The stimulation signal may be generated with such high frequencies.

The implant may have a size and/or shape such that it is implanted in the body of the subject with minimal long-term discomfort. For example, the total volume of the implant is in a range between 1.9 cc and 0.1 cc, 1.8 cc and 0.2 cc, 1.7 cc and 0.3 cc, 1.6 cc and 0.4 cc, 1.5 cc and 0.5 cc, 1.4 cc and 0.6 cc, 1.3 cc and 0.7 cc, 1.2 cc and 0.8 cc, or 1.1 cc and 0.9 cc. The implant may be cylindrical, tubular, or rectangular in shape, for example.

In exemplary embodiments, the implant has a longevity exceeding 5 years in a 1.0 cc volume and is suitable for implantation near the posterior tibial nerve. For example, the enclosure or housing of the implant may be 7 mm in diameter and 25 mm long. In addition to being suitable to treat urinary and/or bowel incontinence, the device design and form factor may be appropriate for other therapies for which intermittent stimulation has been demonstrated effective: Such therapies include, but are not limited to: (a) intermittent sphenopalatine ganglion stimulation (SPGS) for headaches; (b) bilateral supraorbital nerve stimulation (SNSt) for headaches at 20 minutes per day; (c) vagus nerve stimulation for epilepsy and depression at 30 seconds every 5 minutes; (d) PTNS for pelvic pain; and, (e) stimulation in the infraorbital foramina for neuropathic pain.

The implant may be powered in many ways. The battery of the implant may be a primary battery. The circuitry of the implant may have a low current drain such that the primary battery may be effective for many years. The battery of the implant may be rechargeable and may be recharged wirelessly. The recharging power may be furnished from an external (non-implanted) device during a charging period. The implant may have no battery, with power furnished from an external (non-implanted) device when stimulation is required.

One or more of a housing or enclosure of the implant or the electrode array may be anchored into the tissue with a fixation element of the housing or electrode array. The fixation element may comprise a hook, a pin, a screw, a pigtail screw, a ring, a grasper, or a suture, to name a few examples. To position the electrode assembly at or adjacent the sciatic nerve or the branch thereof, the nerve or branch may be encircled with a cuff of the electrode assembly.

In some embodiments, the lead may have rod electrodes as opposed to cuff electrodes. The lead can be implanted with a dilator and introducer. The user can employ an introducer and dilator to tunnel from the incision to a site near the nerve. Then, the user can advance the lead through the introducer and remove the introducer. Following that, the user can employ the blunt dissection tool to tunnel in the other (cranial) direction from the incision and can place the pulse generator there. Consequently, the procedure generally does not expose the stimulation site nor the pulse generator site.

The electrode assembly may at least partially be separated from the housing or enclosure by a lead. The stimulation signal may be unipolar, bipolar, or tripolar. The electrode assembly may comprise a return assembly placed on the exterior of the housing or enclosure of the implant. Alternatively or in combination, at least two electrodes may be on a lead and separated from the housing or enclosure to avoid stimulating muscle at the housing or enclosure.

The pulse generator at the housing or enclosure of the implant may be connected to the lead in many ways. In some embodiments, the lead does not have a connector detachable from the pulse generator, but instead connects permanently to the pulse generator, simplifying construction and improving reliability. In some embodiments, the lead has a connector detachable from the pulse generator. This detachability can allow the user to implant the lead for a qualification period, and then, if qualification is successful, to implant a pulse generator and connect it to the previously-implanted lead. The detachability also can facilitate implantation with a single incision, where the pulse generator is implanted cranial to the incision, and the lead is implanted caudal to the incision.

A wireless communication transceiver of the implant may communicate with an external programmer. In communicating with the wireless communication transceiver, the external programmer may receive one or more of a current of the battery, a voltage of the battery, time, a therapy status, a waveform of the generated stimulation signal, a device orientation, a device alignment, or other implant information or command. The external programmer may display the various statuses of the implant. In some embodiments, the external programmer is in communication with a printing device to record a therapeutic protocol delivered by the implant.

The wireless communication transceiver may communicate with the external programmer through one or more of a Bluetooth connection, a Bluetooth LE connection, a Zigbee connection, a Wi-Fi connection, an IR connection, an RF connection, an ultrasound-based connection, a WiMax connection, an ISM connection, an AM connection, an FM connection, a conductive connection, or a magnetic connection. In many embodiments, the external programmer may send signals to the implant by interfacing with the implant using a magnetic field and the programmer may receive communication signals back electrically conducted from the implant. These conductive communications signals may be generated by the pulse generator so as not to stimulate any nerve, muscle, or other tissue. For example, the communication signal may be one or more of below a threshold stimulation pulse amplitude, below a threshold stimulation pulse duration, or during a refractory period of a nerve, muscle, or other tissue. The generated conductive communication signals may be low power and generated with low current drain, further contributing to the long useful life of the implant.

The external programmer may come in many forms. The external programmer may comprise one or more of a key fob, a smartphone, a smartwatch, a tablet computer, a laptop computer, a wearable computing device, a strap configured to at least partially encircle a limb of the subject, or other portable computing device. For example, the external programmer may comprise a wearable magnetic field generator and the wearable magnetic field generator may be aligned to optimize magnetic communication with the wireless communication transceiver of the implant when worn.

In some embodiments, the external programmer may be used to stimulate tissue and the external programmer may itself comprise a tissue stimulator. For example, the tissue stimulator may comprise one or more of a percutaneous tibial nerve stimulator or a transcatheter electrical nerve stimulator.

The implant may be configured to detect a magnetic field. The generation of the stimulation signal may be postponed, disabled, or otherwise modified in response to the detected magnetic field. The magnetic field may be generated from an external programmer to communicate with the circuitry of the implant. The magnetic field may be detected with a magnetic field sensor such as a giant magnetoresistance (GMR) switch, which is small, light, and reliable. The magnetic field comprises an MRI field. For example, when an MRI field is detected, the implant or at least the stimulation signals generated may be switched off. More typically, the magnetic field sensor may detect signals from the external programmer such as to receive instructions. In addition, the patient or medical professional can apply a permanent magnet in vicinity of the implanted pulse generator, for postponing, modifying, or stopping therapy; for example if therapy becomes unpleasant or ineffective.

An orientation or alignment of the implant may be detected, such as with an accelerometer of the implant. The generation of the stimulation signal may be disabled, postponed, or otherwise modified in response to the detected orientation or movement.

Aspects of the present disclosure may also provide implantable devices for permanent implantation in a body of a subject for long-term use to stimulate tissue. An exemplary device may comprise an enclosure an enclosure configured to be implanted in a body of a subject, circuitry disposed within the enclosure, a battery disposed within the enclosure and coupled to the circuitry, an electrode assembly coupled to the enclosure and the circuitry, and a lead coupling the electrode assembly to the enclosure and separating at least a portion of the electrode assembly from the enclosure. The circuitry may be configured to generate a stimulation signal with a low duty cycle of between 0.1% and 2.5% and a low background current drain of between 0.1 µA and 5 µA. The battery may provide power to the circuitry to generate the stimulation signal. The electrode assembly may be configured to direct the generated stimulation signal to the tissue of the subject. The low duty cycle and low current drain of the generated stimulation signal may combine to provide a useful life of the implantable device implanted in the body of at least 5 years without removal from the body.

The useful life of the implantable device may be in a range of between 5 and 35 years, 6 and 34 years, 7 and 33 years, 8 and 32 years, 9 and 31 years, 10 and 30 years, 11 and 29 years, 12 and 28 years, 13 and 27 years, 14 and 26 years, 15 and 25 years, 16 and 24 years, 17 and 23 years, 18 and 22 years, or 19 and 21 years. The background current drain may be in a range of between 4.5 µA and 0.10 µA, 4.0 µA and 0.10 µA, 3.5 µA and 0.10 µA, 3.0 µA and 0.10 µA, 2.5 µA and 0.10 µA, 2.0 µA and 0.10 µA, 1.5 µA and 0.10 µA, 1.0 µA and 0.10 µA, 0.9 µA and 0.10 µA, 0.8 µA and 0.10 µA, 0.7 µA and 0.10 µA, 0.6 µA and 0.10 µA, 0.5 µA and 0.10 µA, 0.4 µA and 0.10 µA, 0.3 µA and 0.10 µA, or 0.2 µA and 0.1 µA.

The duty cycle of the stimulation signal may in a range of between 2.4% and 0.1%, 2.3% and 0.1%, 2.2% and 0.1%, 2.1% and 0.1%, 2.0% and 0.1%, 1.9% and 0.1%, 1.8% and 0.1%, 1.7% and 0.1%, 1.6% and 0.1%, 1.5% and 0.1%, 1.4% and 0.1%, 1.3% and 0.1%, 1.2% and 0.1%, 1.1% and 0.1%, 1.0% and 0.1%, 0.9% and 0.1%, 0.8% and 0.1%, 0.7% and 0.1%, 0.6% and 0.1%, 0.5% and 0.1%, 0.4% and 0.1%, 0.3% and 0.1%, or 0.2% and 0.1%. For example, the electrode assembly of the implantable device may direct the stimulation signal to the tissue of the subject for about 30 minutes once a week. In some cases, the electrode assembly of the implant may direct the stimulation signal to the tissue of the subject while the subject is asleep. Alternatively or in combination, the stimulation may be applied as the user, patient, or medical professional desires as described above and herein. Any scheduled stimulation can be preprogrammed or modified as necessary in real time, by the user, patient, or medical professional.

The circuitry may be configured to generate the stimulation signal to have a current in a range of between 19 mA and 1 mA, 18 mA and 2 mA, 17 mA and 3 mA, 16 mA and 4 mA, 15 mA and 5 mA, 14 mA and 6 mA, 13 mA and 7 mA, 12 mA and 8 mA, or 11 mA and 9 mA. The generated stimulation signal may be charged balanced. The generated stimulation signal has a stimulation frequency or stimulation pulse rate in a range between 30 Hz and 10 Hz, 29 Hz and 11 Hz, 28 Hz and 12 Hz, 27 Hz and 13 Hz, 26 Hz and 14 Hz, 25 Hz and 15 Hz, 24 Hz and 16 Hz, 23 Hz and 17 Hz, 22 Hz and 18 Hz, or 21 Hz and 19 Hz. For example, the stimulation frequency may be from 20 Hz to 25 Hz, which a range shown to be effective to treat urinary and/or bowel incontinence with tibial nerve stimulation. The generated stimulation signal may have a stimulation pulse width in a range of between 300 µs and 100 µs, 290 µs and 110 µs, 280 µs and 120 µs, 270 µs and 130 µs, 260 µs and 140 µs, 250 µs and 150 µs, 240 µs and 160 µs, 230 µs and 170 µs, 220 µs and 180 µs, or 210 µs and 190 µs. For example, a pulse pattern with 200 µs pulses at 20 Hz may be shown because this pattern has been shown effective for to treat urinary and/or bowel incontinence with tibial nerve stimulation.

In other embodiments, the circuitry may be configured to generate different pulse patterns for different indications. The stimulation pulse patterns may be from 90 to 500 µs at 20 to 100 Hz, which have been shown effective for relief from peripheral nerve pain. For peripheral nerve field stimulation, most patients prefer the frequency to be between 20 and 50 Hz. Anything higher than this range may be felt as a very strong sensation, or cause burning or pinching. Pulse width in the range of 90 to 250 µs may be best tolerated. Stimulation at higher frequencies, e.g. 1200 Hz, have also been shown effective for relief from peripheral nerve pain and may have an additional advantage of not provoking a sensory response in the patient. The circuitry may be configured to generate stimulation signals at these higher frequencies.

The implant may be powered in many ways. The battery may comprise a primary battery. The capacity of the primary battery may be in a range between 360 mAH and 100 mA, 350 mAH and 110 mAH, 340 mAH and 120 mAH, 330 mAH and 130 mAH, 320 mAH and 140 mAH, 310 mAH and 150 mAH, 300 mAH and 160 mAH, 290 mAH and 170 mAH, 280 mAH and 180 mAH, 270 mAH and 190 mAH, 260 mAH and 200 mAH, 250 mAH and 210 mAH, or 240 mAH and 220 mAH, to name a few. The circuitry of the implantable device may have a low current drain such that the primary battery may be effective for many years. The battery of the implant may be rechargeable and may be recharged wirelessly. The recharging power may be furnished from an external (non-implanted) device during a charging period. The implant may have no battery, with power furnished from an external (non-implanted) device when stimulation is required.

The implant may have a size and/or shape such that it is implanted in the body of the subject with minimal long-term discomfort. For example, the total volume of the implant is in a range between 1.9 cc and 0.1 cc, 1.8 cc and 0.2 cc, 1.7 cc and 0.3 cc, 1.6 cc and 0.4 cc, 1.5 cc and 0.5 cc, 1.4 cc and 0.6 cc, 1.3 cc and 0.7 cc, 1.2 cc and 0.8 cc, or 1.1 cc and 0.9 cc. The enclosure may be hermetically sealed. The enclosure may be cylindrical, tubular, or rectangular (e.g., as in a pill box). The enclosure may comprise an insulative outer coating to prevent undesired stimulation of tissue such as muscle. The insulative outer coating may comprise one or more of silicone rubber, parylene, polyurethane, PEEK, PTFE, or ETFE.

In exemplary embodiments, the implant has a longevity exceeding 5 years in a 1.0 cc volume and is suitable for implantation near the posterior tibial nerve. For example, the enclosure or housing of the implant may be 7 mm in diameter and 25 mm long. In addition to being suitable to treat urinary and/or bowel incontinence, the device design and form factor may be appropriate for other therapies for which intermittent stimulation has been demonstrated effective: Such therapies include, but are not limited to: (a) intermittent sphenopalatine ganglion stimulation (SPGS) for headaches; (b) bilateral supraorbital nerve stimulation (SNSt) for headaches at 20 minutes per day; (c) vagus nerve stimulation for epilepsy and depression at 30 seconds every 5 minutes; (d) PTNS for pelvic pain; and, (e) stimulation in the infraorbital foramina for neuropathic pain.

The electrode assembly may be separated from the enclosure by the lead by a distance in a range between 15 cm and 0.1 mm, 14 cm and 0.1 mm, 13 cm and 0.1 mm, 12 cm and 0.1 mm, 11 cm and 0.1 mm, 10 cm and 0.1 mm, 9 cm and 0.1 mm, 8 cm and 0.1 mm, 7 cm and 0.1 mm, 6 cm and 0.1 mm, 5 cm and 0.1 mm, 4 cm and 0.1 mm, 3 cm and 0.1 mm, 2 cm and 0.1 mm, or 1 cm and 0.1 mm. At least a portion of the lead may be insulated.

One or more of the electrode assembly or enclosure may comprise a fixation element to anchor into the tissue, thereby reducing migration of the implantable device during long-term use in the subject. The fixation element may comprise a hook, a pin, a screw, a pigtail screw, a ring, a grasper, a suture, a tine, or a cuff, to name a few examples.

The electrode assembly may be configured for permanent placement adjacent the tissue. At least a portion of the electrode assembly may be configured for placement adjacent a nerve of the subject. The electrode assembly may comprise an insulative assembly body (e.g., to minimize undesired stimulation to undesired tissue such as muscle where the body may be implanted) and at least one electrode. The electrode(s) may comprise a unipolar electrode, bipolar electrodes, or tripolar electrodes.

The pulse generator at the housing or enclosure of the implant may be connected to the lead in many ways. One or more of the lead or the electrode assembly comprises a connector removably coupling the electrode assembly to the lead or the enclosure. In some embodiments, the lead does not have a connector detachable from the pulse generator, but instead connects permanently to the pulse generator, simplifying construction and improving reliability. In some embodiments, the lead has a connector detachable from the pulse generator. This detachability can allow the user to implant the lead for a qualification period, and then, if qualification is successful, to implant a pulse generator and connect it to the previously-implanted lead. The detachability also can facilitate implantation with a single incision, where the pulse generator is implanted cranial to the incision, and the lead is implanted caudal to the incision. In some embodiments, the lead comprises an inductor configured to act as an RF trap. In some embodiments, the electrode assembly comprises a return electrode disposed on or integral with the enclosure.

The circuitry may comprise a wireless communication transceiver configured to wirelessly communicate with an external programmer. The wireless communication transceiver of the circuitry may be configured to receive instructions from the external programmer to one or more of activate, schedule, modify, modulate, monitor, or end a therapeutic protocol. The wireless communication transceiver may communicate with the external programmer through one or more a Bluetooth connection, a Bluetooth LE connection, a Zigbee connection, a Wi-Fi connection, an IR connection, an RF connection, an ultrasound-based connection, a WiMax connection, an ISM connection, an AM connection, an FM connection, a conductive connection, or a magnetic connection. The wireless communication transceiver of the circuitry may communicate with the external programmer through a conductive connection. The wireless communication transceiver may be configured to generate a communication signal received by the external programmer, the communication signal being one or more of below a threshold stimulation pulse amplitude, below a threshold stimulation pulse duration, or during a refractory period of a nerve.

The external programmer may comprise one or more of a key fob, a smartphone, a smartwatch, a tablet computer, a laptop computer, a wearable computing device, a wand, a strap configured to at least partially encircle a limb of the subject, or other portable computing device. The external programmer may be in communication with a printing device to record a therapeutic protocol delivered by the implantable device.

The external programmer may comprise a wearable magnetic field generator. The wearable magnetic field generator may be aligned with the implantable device to optimize magnetic communication with the wireless communication transceiver of the implantable device when worn.

The external device may comprise a tissue stimulator. The tissue stimulator may comprise one or more of a percutaneous tibial nerve stimulator or a transcutaneous electrical nerve stimulator. The wireless communication transceiver may be configured to communicate to the external programmer one or more of a current status of the battery, a voltage status of the battery, time, a therapy status, a waveform of the generated stimulation signal, a device orientation, a device alignment, or other implantable device information or command.

The implantable device may be configured to detect a magnetic field. The generation of the stimulation signal may be postponed, disabled, or otherwise modified in response to the detected magnetic field. The magnetic field may be generated from an external programmer to communicate with the circuitry of the implantable device. The magnetic field may be detected with a magnetic field sensor such as a giant magnetoresistance (GMR) switch, which is small, light, and reliable. The magnetic field comprises an MRI field. For example, when an MRI field is detected, the implant or at least the stimulation signals generated may be switched off. More typically, the magnetic field sensor may detect signals from the external programmer such as to receive instructions. In addition, the patient or medical professional can apply a permanent magnet in vicinity of the implanted pulse generator, for postponing, modifying, or stopping therapy; for example if therapy becomes unpleasant or ineffective.

The implantable device may further comprise an accelerometer coupled to the circuitry. The accelerometer may be configured to detect an orientation or alignment of the implantable device or a movement of the subject. The circuitry may be configured to disable, postpone, or otherwise modify a therapeutic protocol of the implantable device in response to the detected orientation, alignment, or movement.

While the present disclosure describes neuromodulation for overactive bladder (OAB) or bowel incontinence (BI) at a branch of the sciatic nerve and more particularly the posterior tibial nerve, the implantable device may be suitable to stimulate many other tissues and treat many other conditions. Alternatively or in combination for OAB or BI, the implantable device may more particularly target a sural nerve, pudendal nerve, or superficial peroneal nerve, all of which are branches of the sciatic nerve. An advantage to targeting these target nerves or branches may include ease of access. The implantable device may also provide clinical utility for treatment of acute pain, chronic pain, hypertension, congestive heart failure, gastro-esophageal reflux, obesity, erectile dysfunction, insomnia, a movement disorder, or a psychological disorder. In particular for treatment of peripheral nerve pain, the implantable device could target one or more of the following: greater occipital nerve, tibial nerve, superficial peroneal nerve, saphenous nerve, Intercostal nerve, or other peripheral nerve of the subject. Another application of the implantable device may be stimulating the ileo-inguinal nerve for pain following hernia surgery, or the genitofemoral nerve for relief of post-vasectomy pain, which is an untreated problem in tens of thousands of patients. Some IC (interstitial cystitis) patients with pelvic pain may also be responsive to PTNS.

In other examples, the electrode assembly may be configured to direct the generated stimulation signal to one or more of a greater occipital nerve, a tibial nerve, a superficial peroneal nerve, a saphenous nerve, an intercostal nerve, a subcostal nerve, a lumbar plexus, a sacral plexus, a femoral nerve, a pudendal nerve, a sciatic nerve, a femoral nerve, a deep peroneal nerve, a common peroneal nerve, an ulnar nerve, an obturator nerve, a genitofemoral nerve, an iliohypogastric nerve, a median nerve, a radial nerve, a musculocutaneous nerve, a brachial plexus, or other peripheral nerve of the subject. The generated stimulation signal may be configured to treat one or more of urinary incontinence, bowel incontinence, acute pain, chronic pain, hypertension, congestive heart failure, gastro-esophageal reflux, obesity, erectile dysfunction, insomnia, a movement disorder, or a psychological disorder.

Aspects of the present disclosure may also provide methods for stimulating tissue with an implant permanently implanted in a body of a subject for long-term use. The implant may comprise the implant described above and herein. The implant implanted in a body of a subject may be powered with a battery. The battery may be enclosed in an enclosure of the implant. The implant may have a low background current drain between 0.1 µA and 5 µA from the primary battery. A stimulation signal may be generated with circuitry enclosed in the enclosure. The circuitry may generate the stimulation signal with a low duty cycle of between 0.1% and 2.5%, or other low duty cycles or current drains. The stimulation signal may be directed to tissue of the subject with an electrode array at least partially separated from the enclosure of the implant by a lead coupling the electrode array with the circuitry within the enclosure. As described above and herein, the low duty cycle and low current drain of the generated stimulation pulse combine to provide a useful life of the implantable device implanted in the body of at least 5 years without removal from the body. The implant may be used in many ways, configured in many ways, and include a variety of features as described above and herein.

Aspects of the present disclosure may also provide methods for improving a urinary or bowel function in a subject. An incision may be created in a leg of a patient. A first tunnel may be created in the leg of the patient through the incision. A second tunnel may be created in the leg of the patient through the incision. One or more of the first or second tunnels may be created with a blunt dissection tool as described above and herein. An implantable pulse generator may be placed in the first tunnel. At least a portion of an electrode assembly may be placed in the second tunnel so that the electrode assembly is positioned at or adjacent a sciatic nerve or a branch thereof such as by at least partially encircling the sciatic nerve or branch thereof with a cuff of the electrode assembly. The implantable pulse generator and the electrode assembly may be coupled to one another. Together, the implantable pulse generator and the electrode assembly may comprise an implant or implantable device as described above and herein. One or more of the implantable pulse generator or the electrode assembly may be fixated to the first or second tunnel, respectively, such as by anchoring a fixation element of the implantable pulse generator or the electrode assembly to the first or second tunnels, respectively. The incision may be closed. The implantable pulse generator may generate a stimulation signal and the electrode assembly may direct the stimulation signal to the tissue of the subject. The stimulation signal may improve the urinary or bowel function in the subject. As described above and herein, the implantable pulse generator may generate a stimulation signal with a low duty cycle of between 0.1% and 2.5% and a low background current drain of between 0.1 µA and 5 µA, or other low duty cycles and/or low current drains. As described above and herein, the implantable pulse generator and the electrode assembly may be implanted in the body for at least 5 years without removal from the body or losing function.

Aspects of the present disclosure may also provide methods for improving a urinary or bowel function in a subject. A primary incision may be created in a leg of a patient. A secondary incision may be created in the leg of the patient. A tunnel between the first and second incisions may be created in the leg of the patient. The tunnel may be created with a blunt dissection tool as described above and herein. A pulse generator of an implant may be advanced through the primary incision to be positioned at or near the stimulation site. At least a portion of an electrode assembly of the implant may be advanced through the secondary incision to be positioned at or adjacent a sciatic nerve or a branch thereof such as by at least partially encircling the sciatic nerve or branch thereof with a cuff of the electrode assembly. The pulse generator and the portion of the electrode assembly may be coupled to one another through a lead positioned in the tunnel. The implant may be fixated through one or more of the primary or secondary incisions such as by anchoring a fixation element of the implantable pulse generator or the electrode assembly to the first or second tunnels. The primary and secondary incisions may be closed. The electrode assembly of the implant may direct a stimulation signal to the tissue of the subject. The stimulation signal may improve the urinary or bowel function in the subject. As described above and herein, the implantable pulse generator may generate a stimulation signal with a low duty cycle of between 0.1% and 2.5% and a low background current drain of between 0.1 µA and 5 µA, or other low duty cycles and/or low current drains. As described above and herein, the implantable pulse generator and the electrode assembly may be implanted in the body for at least 5 years without removal from the body or losing function.

Aspects of the present disclosure provide system for stimulating tissue. An exemplary system may comprise an implantable pulse generator, an electrode assembly, and an external programmer. The implantable pulse generator may be configured to be implanted in a patient. The implantable pulse generator may comprise circuitry to generate a stimulation signal and receive a wireless signal. The electrode assembly may be configured to be implanted in the patient. The electrode assembly may be configured to direct the stimulation signal generated by the implantable pulse generator to tissue of the patient. The external programmer may be configured to generate the wireless signal received by the implantable pulse generator. The stimulation signal may be generated by the implantable pulse generator in response to the wireless signal. As described above and herein, the implantable pulse generator may generate a stimulation signal with a low duty cycle of between 0.1% and 2.5% and a low background current drain of between 0.1 µA and 5 µA, or other low duty cycles and/or low current drains. As described above and herein, the implantable pulse generator and the electrode assembly may be implanted in the body for at least 5 years without removal from the body or losing function.

In many embodiments, the implantable pulse generator may comprise a primary battery. In other embodiments, an external power source may be needed. The system may further comprise an external power source configured to wirelessly provide power to the implantable pulse generator. The external power source may provide power to the implantable pulse generator magnetically, inductively, ultrasonically, or with RF power transmission. The external power source may be configured to wirelessly recharge a rechargeable power cell of the implantable pulse generator. The external programmer may comprise the external power source.

The external programmer (e.g., the "wand") may comprise a relay configured to receive a first signal from a separate control device and transmit the wireless signal to the implantable pulse generator in response to the received first signal. The separate control device may be user operated for display and control. The separate control device may comprise one or more of a key fob, a smartphone, a smartwatch, a tablet computer, a laptop computer, a wearable computing device, or other portable computing device. The separate control device may comprise a wearable magnetic field generator. The wearable magnetic field generator may be aligned to optimize magnetic communication with a wireless communication transceiver of the implantable pulse generator when worn. In some embodiments, the user or subject may choose between using only the relay, the separate control device, or both. For instance, the relay may include controls and a display to interface with the implant.

The external programmer or relay may be in communication with the separate control device and the external programmer or relay may be in communication with the implantable device through one or more of a Bluetooth connection, a Bluetooth LE connection, a Zigbee connection, a Wi-Fi connection, an IR connection, an RF connection, an ultrasound-based connection, a WiMax connection, an ISM connection, an AM connection, an FM connection, a conductive or a magnetic connection. For instance, the wireless communication transceiver of the circuitry may communicate with the external programmer through a conductive connection, and the wireless communication transceiver may be configured to generate a communication signal received by the external programmer. These conductive communications signals may be generated by the pulse generator so as not to stimulate any nerve, muscle, or other tissue. The communication signal may be one or more of below a threshold stimulation pulse amplitude, below a threshold stimulation pulse duration, or during a refractory period of a nerve. Generally, the communication between the relay and the separate control device may be relatively high power and the communication between the implant and the relay may be relative low power and short range. Accordingly, the separate control device may be placed in a convenient location with the user while not compromising the low power requirements of the implant.

In some embodiments, the implantable device communicates directly with the external programmer without any relay. The external programmer may comprise one or more of a key fob, a smartphone, a smartwatch, a tablet computer, a laptop computer, a wearable computing device, a strap configured to at least partially encircle a limb of the subject, or other portable computing device. The external programmer may comprise a general use computing device (e.g., a tablet computer) having software therein to communicate with the implant. Alternatively or in combination, the external programmer or wand may itself include controls and displays, such that another computing device may not be necessary.

In some embodiments, the external programmer is in communication with a printing device to record a therapeutic protocol delivered by the implantable device.

In some embodiments, the external device comprises a tissue stimulator. The tissue stimulator may be configured to deliver a signal to the tissue of the subject through a percutaneously or transcutaneously implanted needle or electrode. The needle or electrode may be implanted temporarily such as to qualify the subject or patient for the system. The subject or patient may be qualified for use of the system in many ways for a variety of reasons as described above and herein.

The external programmer may be configured to receive one or more of a current status of the battery, a voltage status of the battery, time, a therapy status, a waveform of the generated stimulation signal, a device orientation, a device alignment, or other implantable device information or command.

The external programmer may comprise an easy to use user interface. For example, the external programmer may comprise a single control button and the external programmer may be operable from the single control button. The external programmer may be differently responsive to a single short press of the single control button, a double short press of the single control button, and a hold of the single control button. In some embodiments, the external programmer may comprise a display or indicator light which, for example, indicates an active wireless connection between the external programmer and the implantable pulse generator. The wireless signal received by the implantable pulse generator may be configured to one or more of activate, schedule, postpone, modify, modulate, monitor, or end a therapeutic protocol.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

To provide further clarity to the Detailed Description and associated Figures, the following list of components and associated reference numbers is provided. Like reference numbers refer to like elements.

Figure 1:
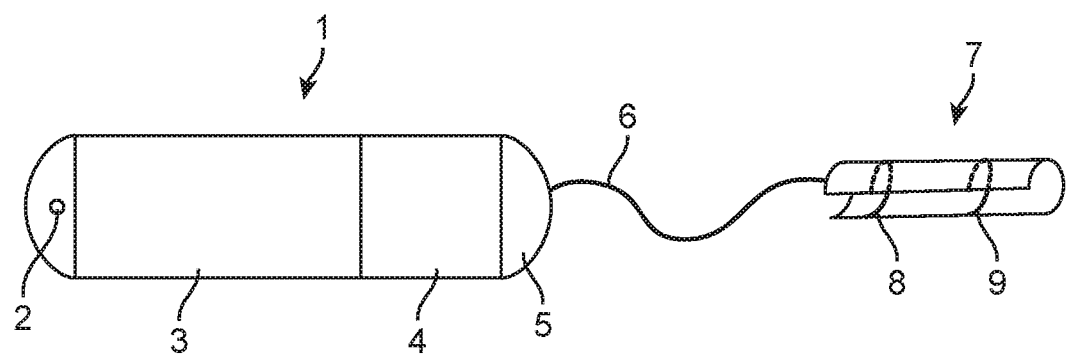
FIG. 1 shows a side view of a bipolar miniature implanted neurostimulator having a cuff electrode assembly, according to many embodiments.
Figure 2:
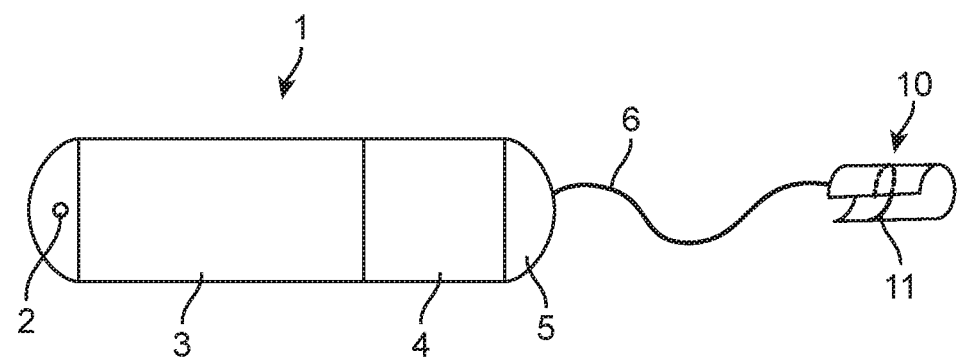
FIG. 2 shows a side view of a unipolar miniature implanted neurostimulator having a cuff electrode assembly, according to many embodiments.
Figure 3:
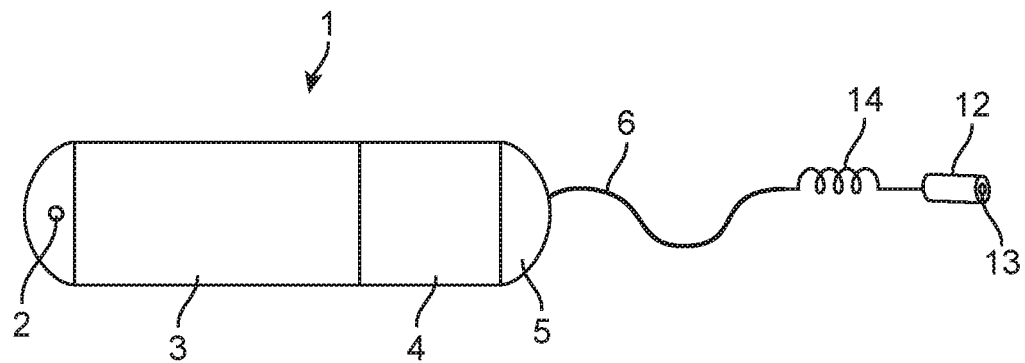
FIG. 3 shows a side view of a unipolar miniature implanted neurostimulator with an RF trap and a rod electrode assembly, according to many embodiments.
Figure 4:
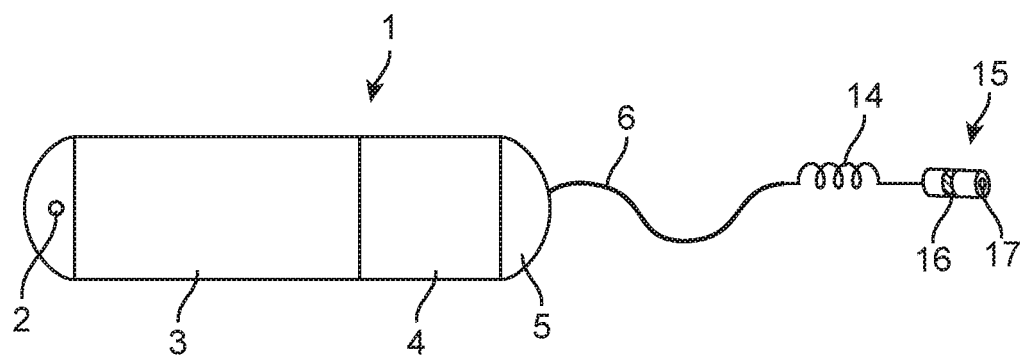
FIG. 4 shows a side view of a bipolar miniature implanted neurostimulator with an RF trap and a rod electrode assembly, according to many embodiments.
Figure 5:
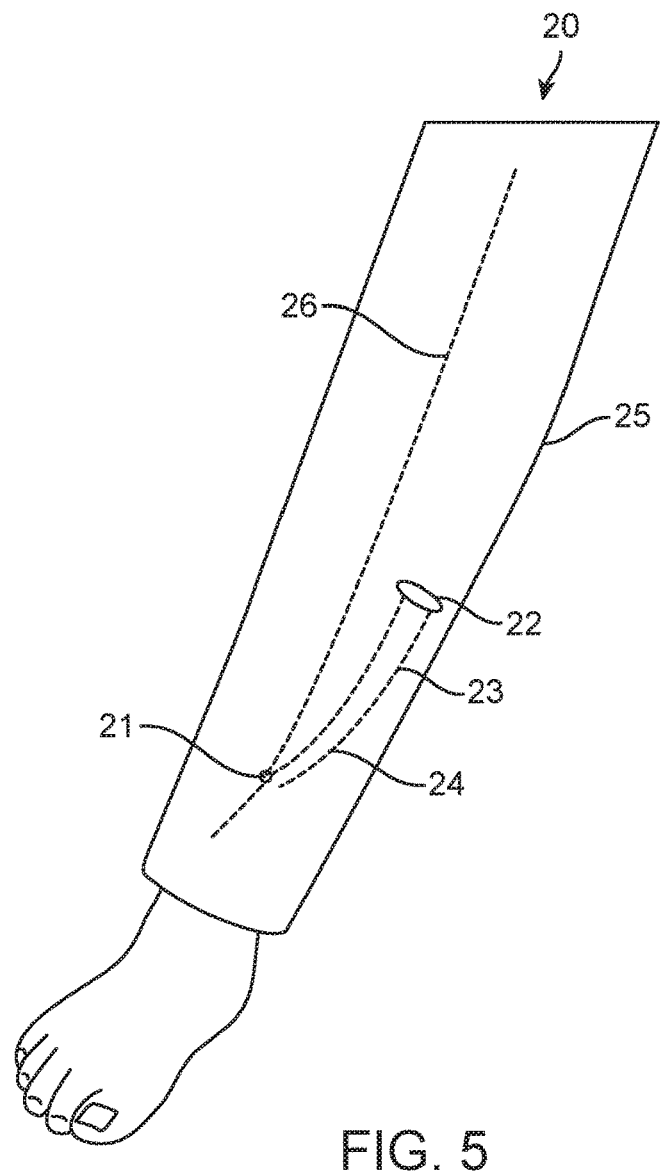
FIG. 5 shows a perspective view of a lower leg of a subject having a tunnel made therein for the implantation of a miniature implanted neurostimulator, according to many embodiments.
Figure 6:
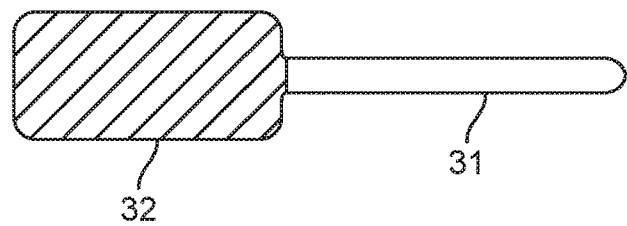
FIG. 6 shows a side view of a blunt dissection tool, according to many embodiments.
Figure 7:
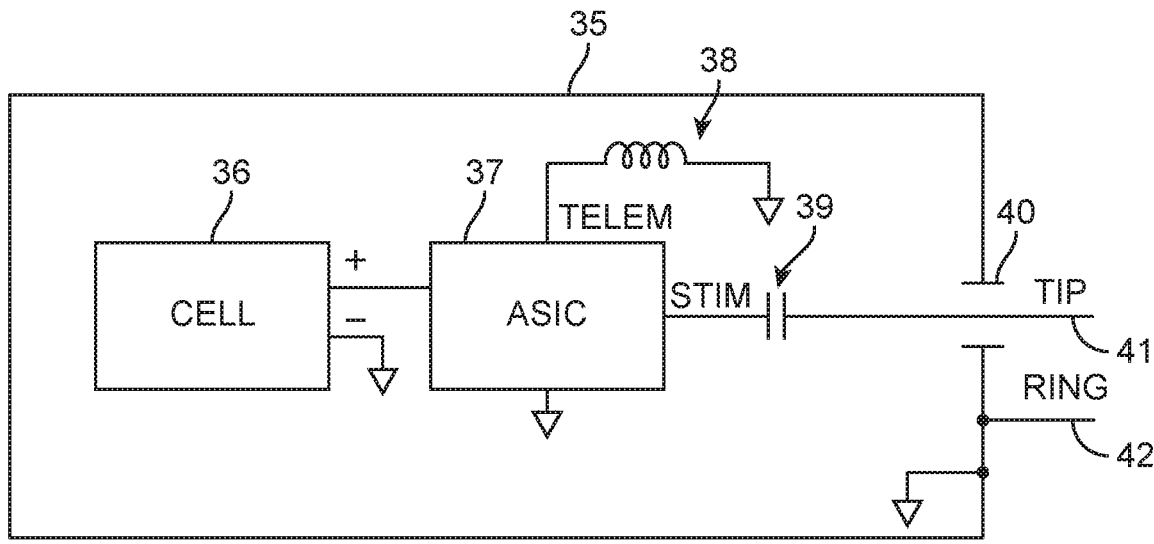
FIG. 7 shows a block diagram for a miniature implanted neurostimulator with inductive telemetry, according to many embodiments.
Figure 20:
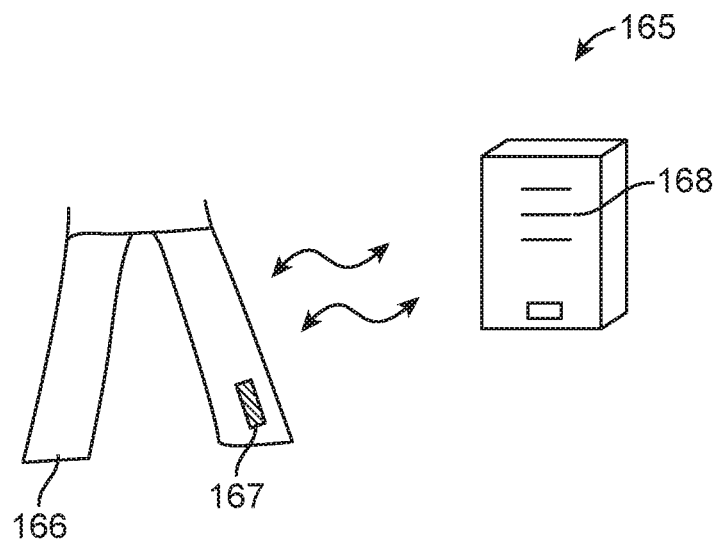
FIG. 20 shows a schematic of a key fob programmer for miniature implanted neurostimulators, according to many embodiments.
Figure 30:
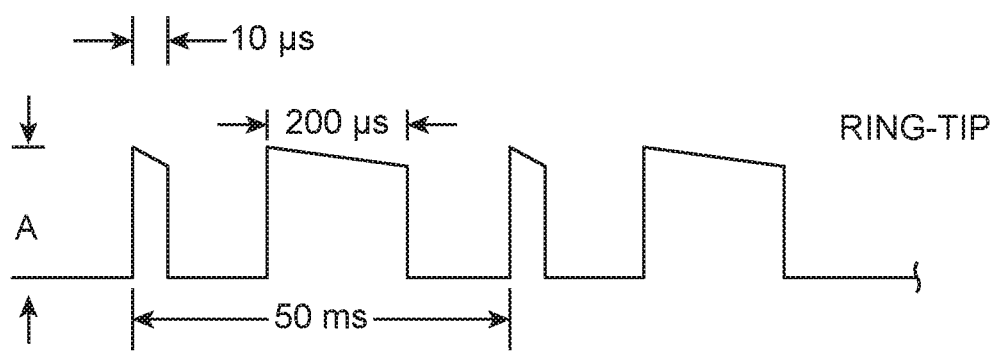
FIG. 30 shows a graph of implant marker synchronization pulses during stimulation, accordingly to many embodiments.
Figure 35:
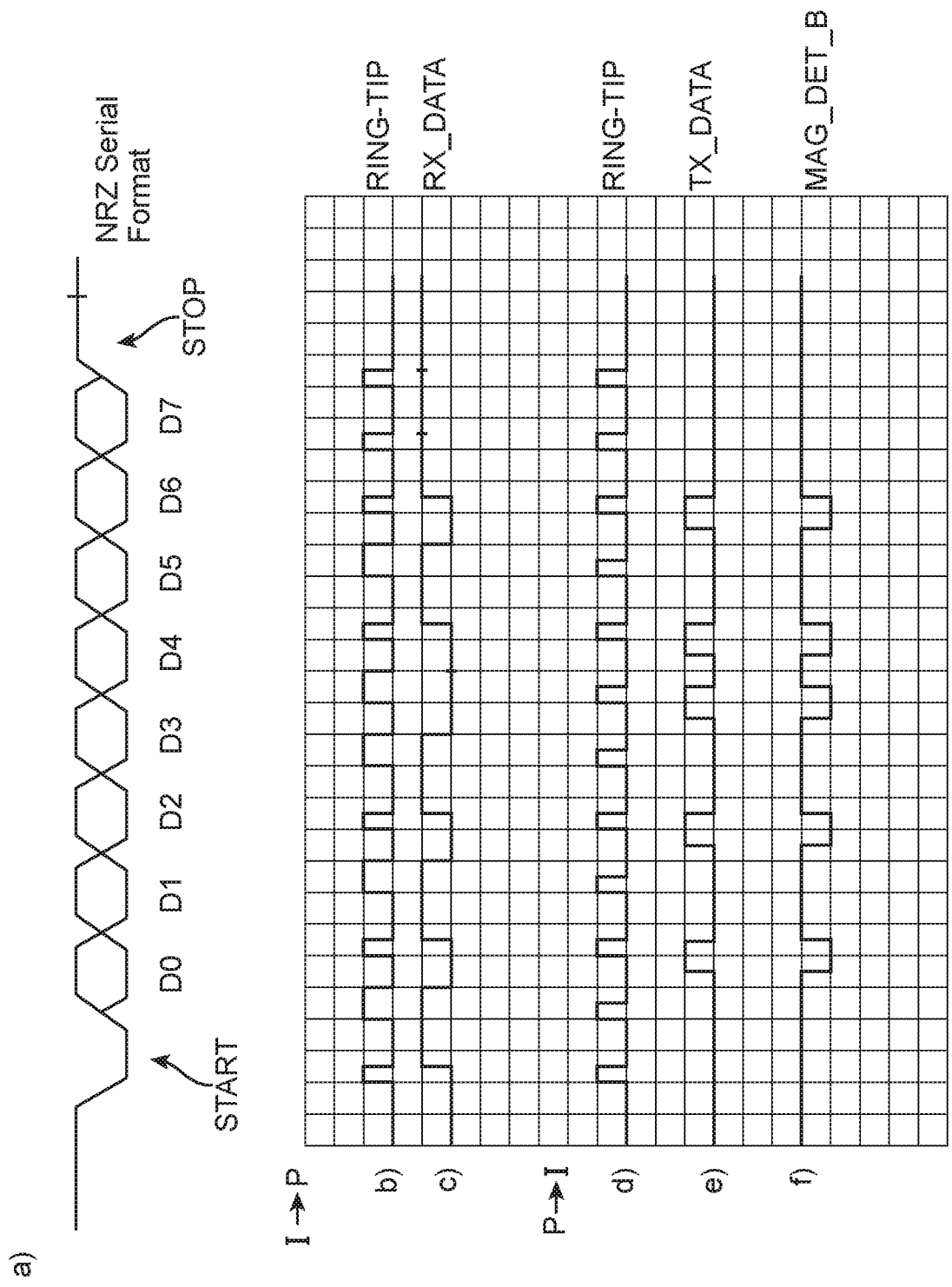
FIG. 35 shows a graph of a telemetry data format, according to many embodiments.

FIG. 1
1—miniature implanted neurostimulator
2—anchor feature
3—cell compartment
4—electronics compartment
5—header
6—flexible insulated lead wires
7—bipolar cuff electrode assembly
8—proximal cuff electrode
9—distal cuff electrode FIG. 2
1—miniature implanted neurostimulator
2—anchor feature
3—cell compartment
4—electronics compartment
5—header
6—flexible insulated lead wire
10—unipolar cuff electrode assembly
11—distal cuff electrode FIG. 3
1—miniature implanted neurostimulator
2—anchor feature
3—cell compartment
4—electronics compartment
5—header
6—flexible insulated lead wire
12—rod electrode assembly
13—distal rod electrode
14—inductor FIG. 4
1—miniature implanted neurostimulator
2—anchor feature
3—cell compartment
4—electronics compartment
5—header
6—flexible insulated lead wire
14—inductor
15—bipolar rod electrode assembly
16—proximal rod electrode
17—distal rod electrode FIG. 5
20—single incision surgical procedure
21—stimulation site
22—incision
23—tunnel for generator
24—tunnel for electrode assembly
25—leg
26—nerve FIG. 6
30—blunt dissection tool
31—rod
32—handle FIG. 7
35—block diagram, miniature implanted neurostimulator with inductive telemetry
36—cell
37—ASIC
38—telemetry coil
39—DC blocking capacitor
40—hermetic feedthrough
41—TIP (cathodic stimulator output)
42—RING (anodic stimulator output)

Figure 8:
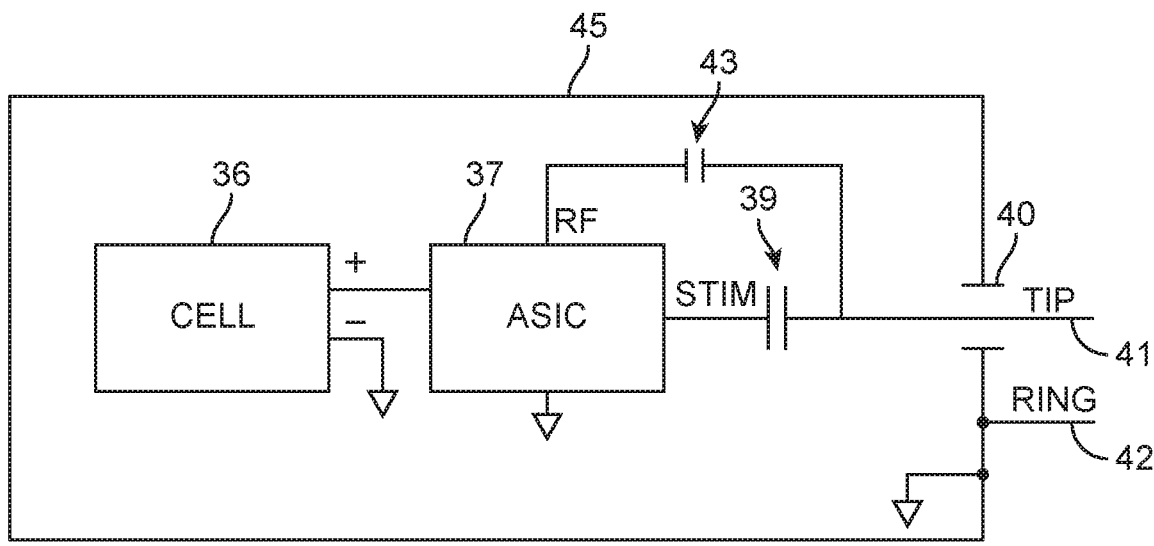
FIG. 8 shows a block diagram for a miniature implanted neurostimulator with radiofrequency (RF) telemetry, according to many embodiments.

FIG. 8
45—block diagram, miniature implanted neurostimulator with RF telemetry

Figure 9:
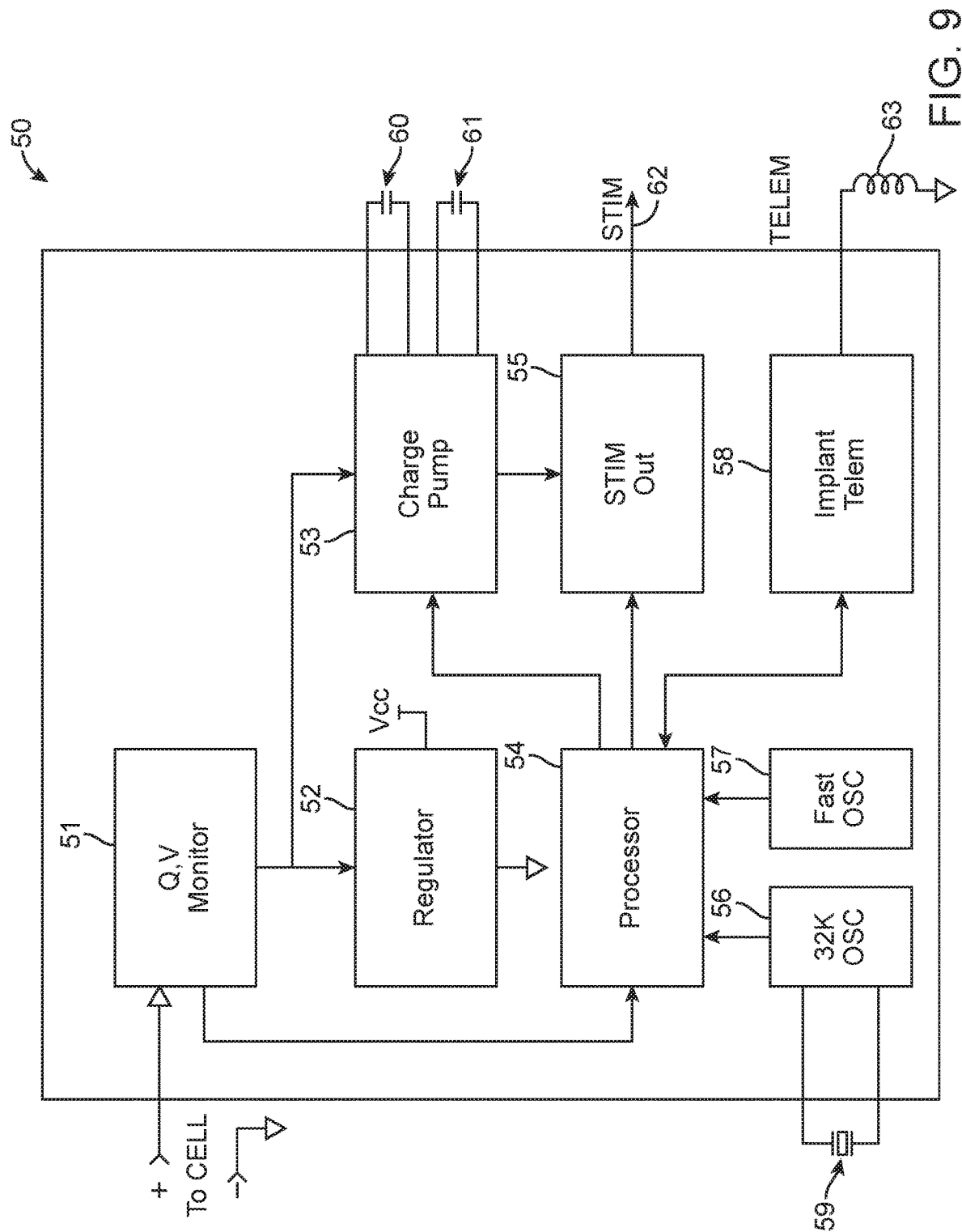
FIG. 9 shows a block diagram of an application specific integrated circuit (ASIC) usable for miniature implanted neurostimulators, according to many embodiments.
Figure 10:
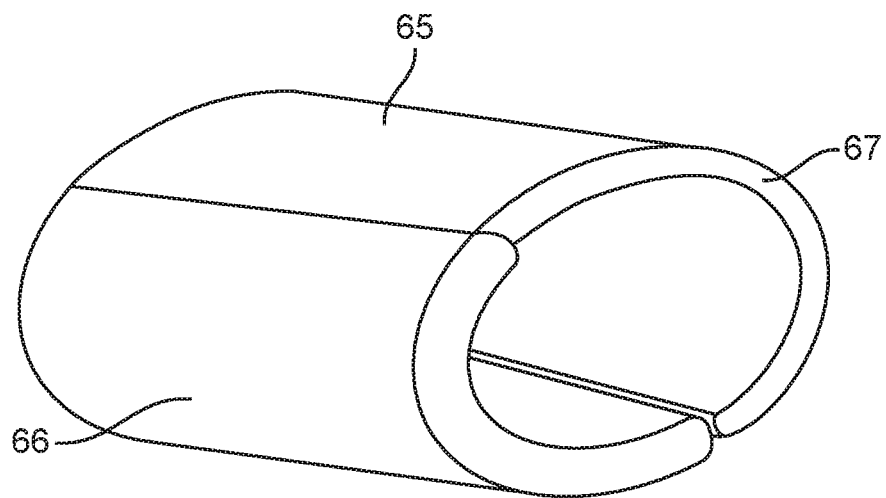
FIG. 10 shows a wearable programmer or limb wand for miniature implanted neurostimulators, according to many embodiments.
Figure 11:
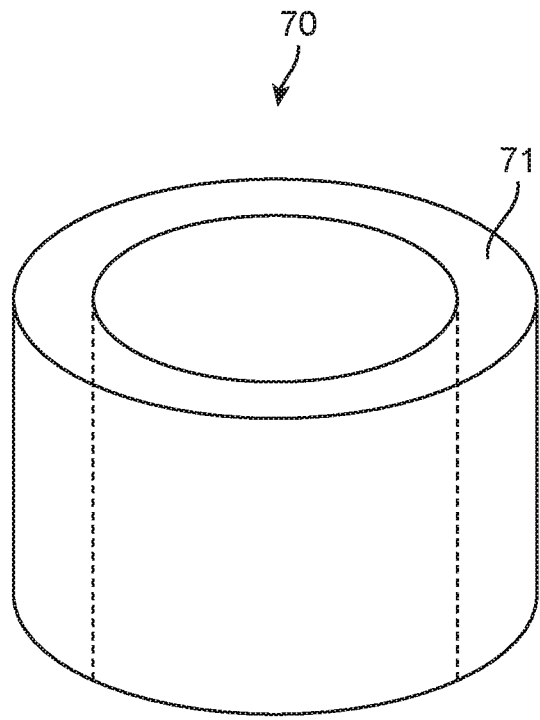
FIG. 11 shows another wearable programmer or limb wand for miniature implanted neurostimulators, according to many embodiments.
Figure 12:
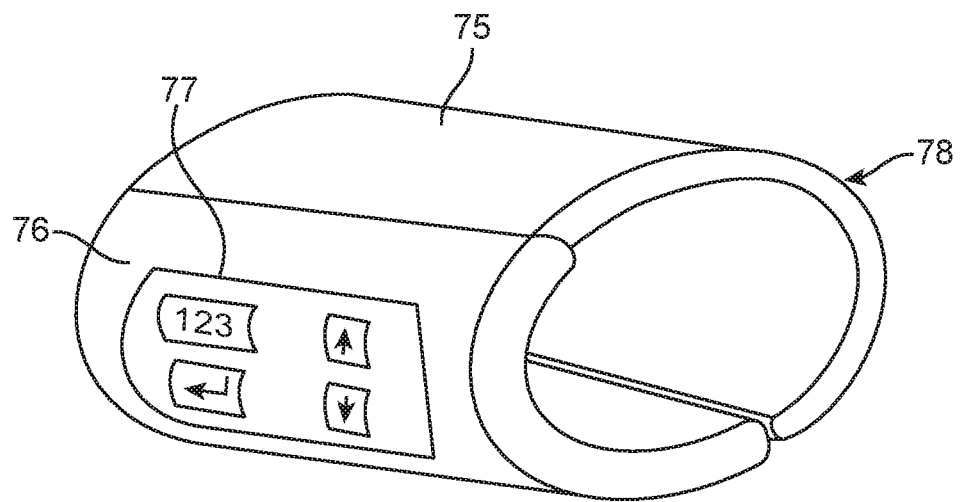
FIG. 12 shows a wearable programmer or limb wand having onboard control(s) and display(s), according to many embodiments.
Figure 13:
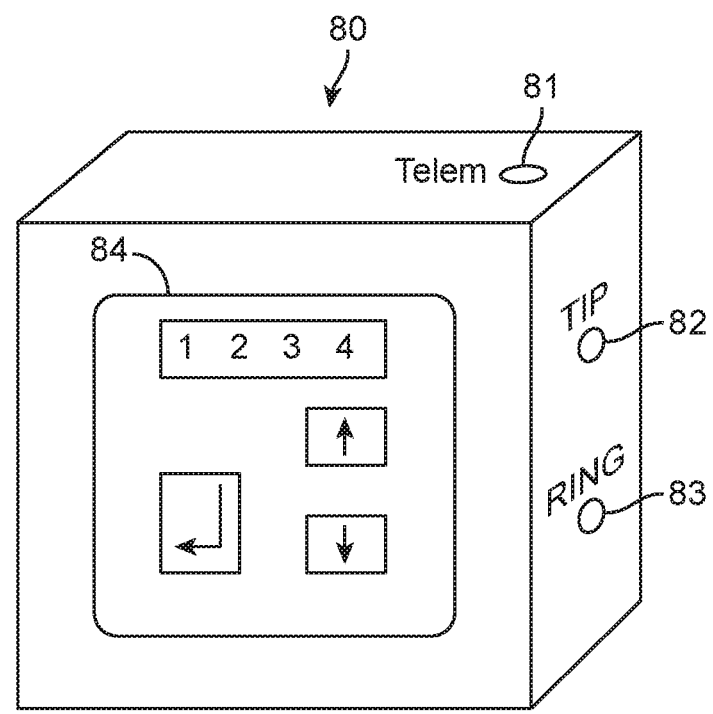
FIG. 13 shows another wearable programmer having onboard control(s) and display(s), according to many embodiments.
Figure 14:
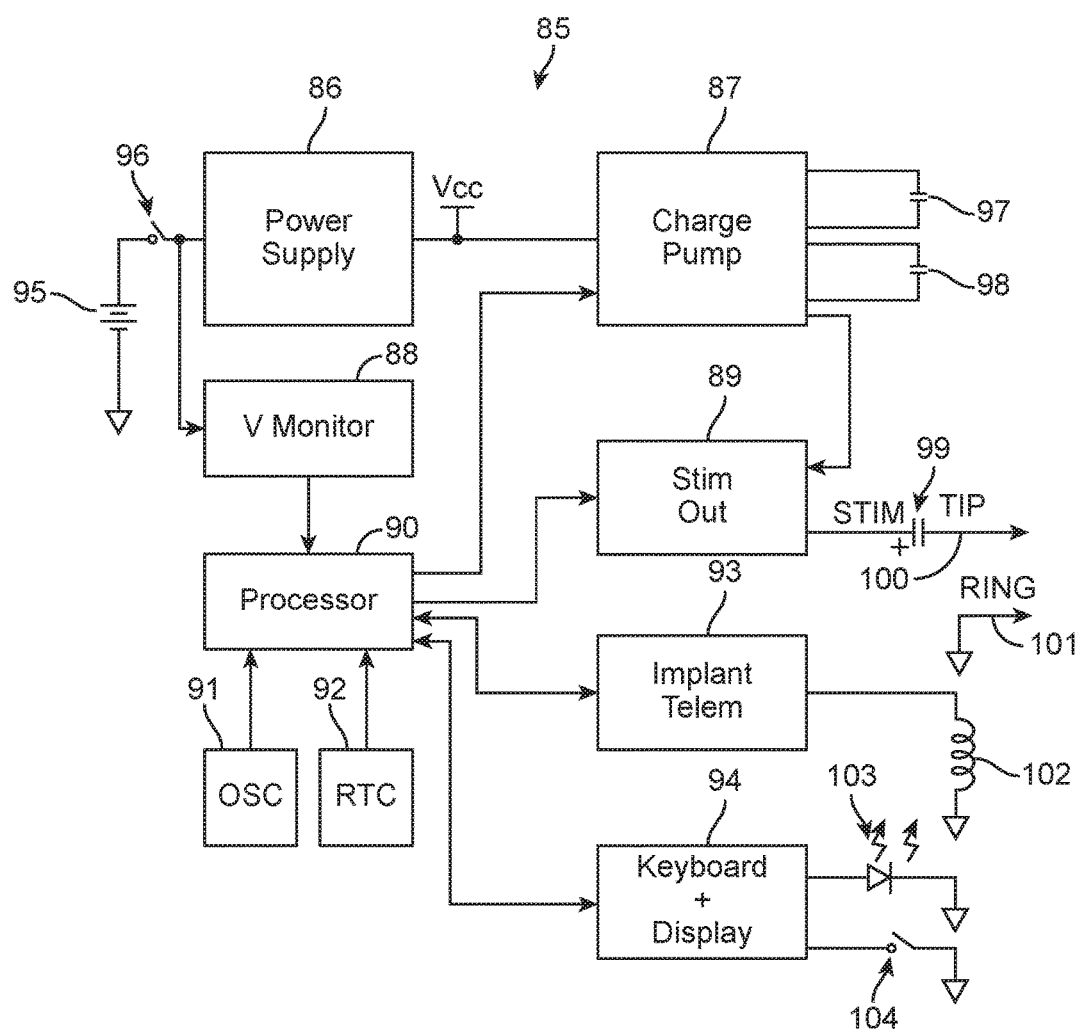
FIG. 14 shows a block diagram for the components of a wearable programmer or limb wand having an onboard (percutaneous tibial neurostimulation) PTNS generator, according to many embodiments.
Figure 15:
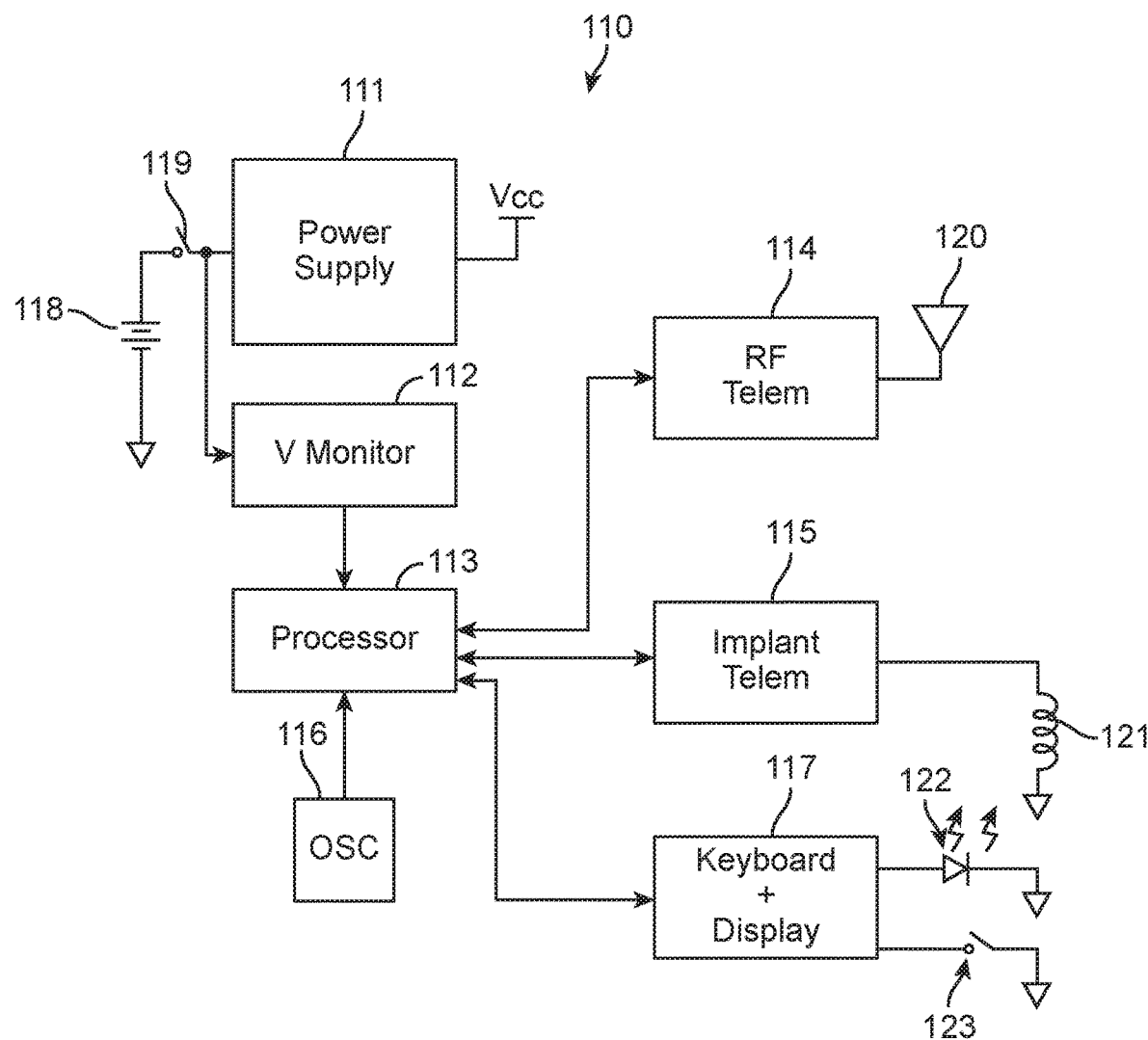
FIG. 15 shows a block diagram for the components of a wearable programmer or limb wand, according to many embodiments.
Figure 16:
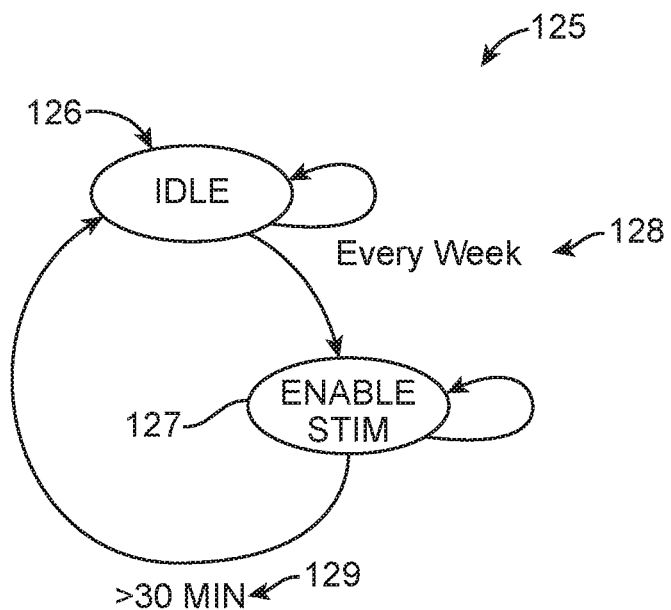
FIG. 16 shows a state diagram for a low duty-cycle stimulator with a scheduled therapy, according to many embodiments.
Figure 17:
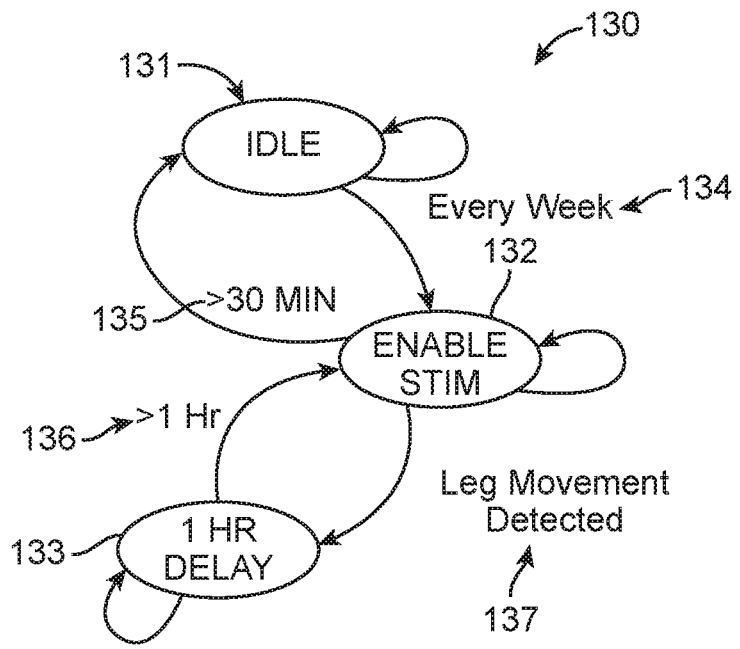
FIG. 17 shows a state diagram for a low duty-cycle stimulator with deferred therapy, according to many embodiments.
Figure 18:
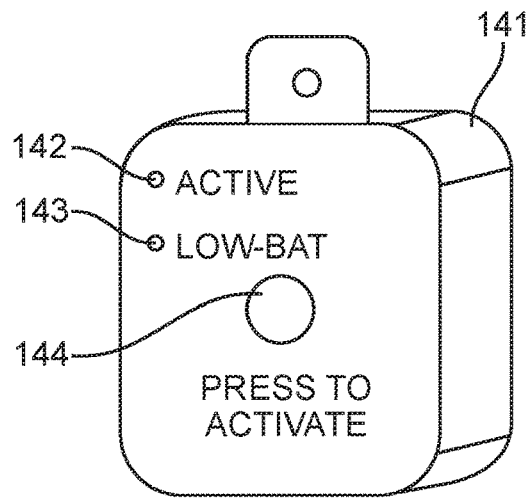
FIG. 18 shows a front view of a patient operated key fob programmer, according to many embodiments.
Figure 19:
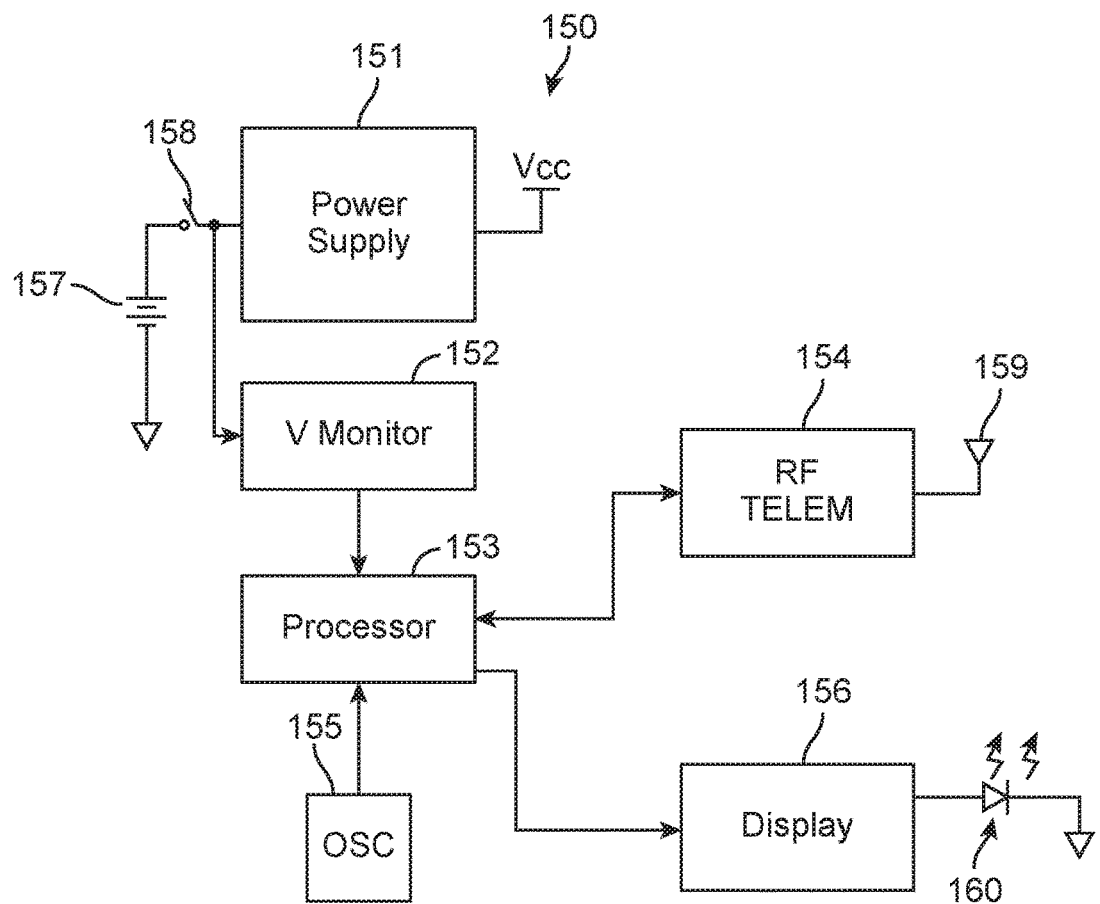
FIG. 19 shows a block diagram for the patient operated key fob of FIG. 18.
Figure 21:
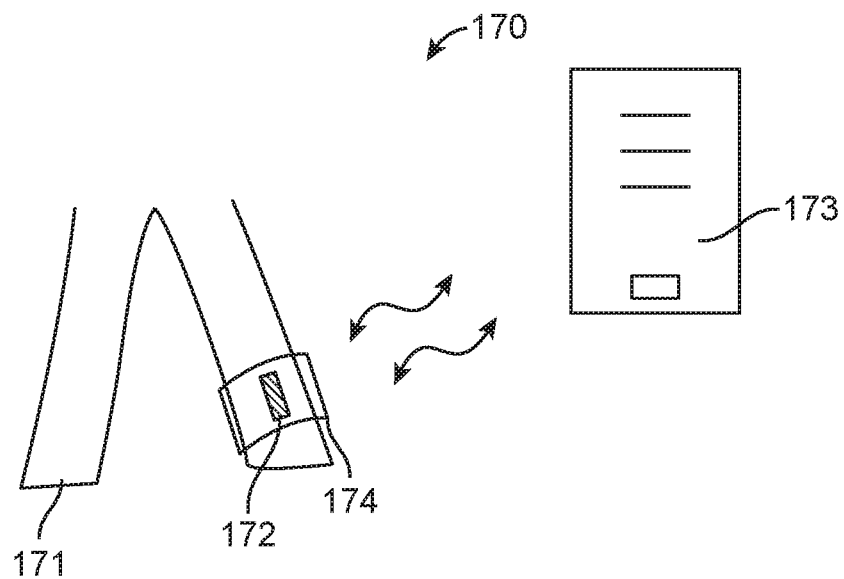
FIG. 21 shows a schematic of a smartphone programmer system for miniature implanted neurostimulators, according to many embodiments.
Figure 22:
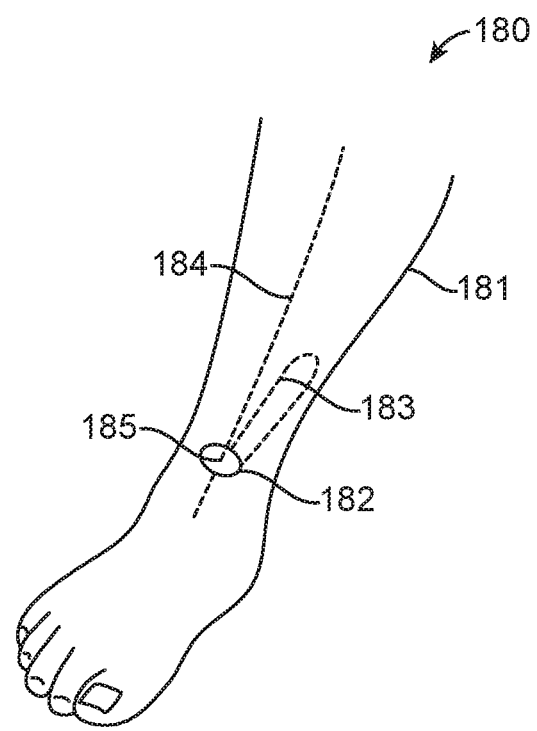
FIG. 22 shows a perspective view of a lower leg of a subject having a tunnel made therein for the implantation of a miniature implanted neurostimulator, according to many embodiments.
Figure 23:
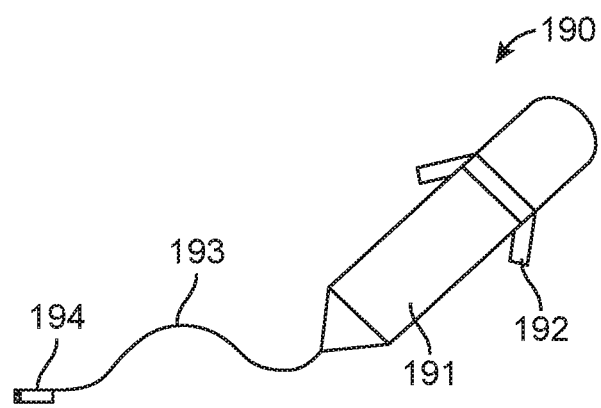
FIG. 23 shows a side view of a miniature implanted neurostimlator having an anchor to prevent migration, according to many embodiments.
Figure 24:
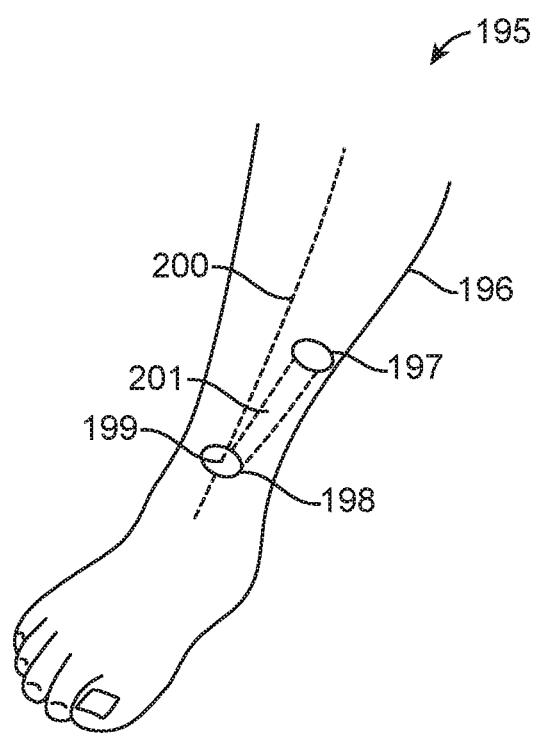
FIG. 24 shows a perspective view of a lower leg of a subject having two tunnels made therein for the implantation of a miniature implanted neurostimulator, according to many embodiments.
Figure 25:
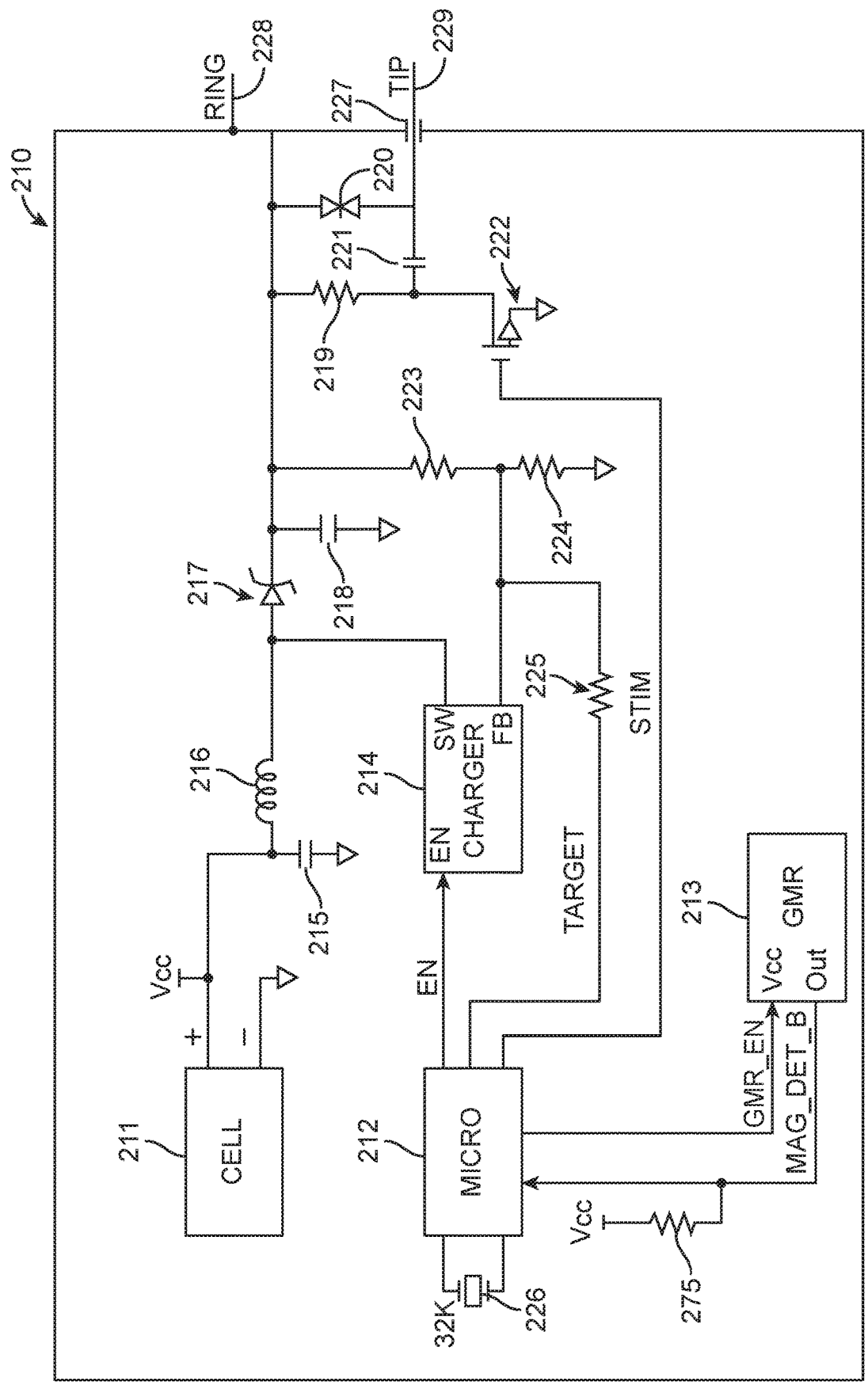
FIG. 25 shows a block diagram of a miniature implanted neurostimulator with hybrid telemetry, according to many embodiments.
Figure 26:
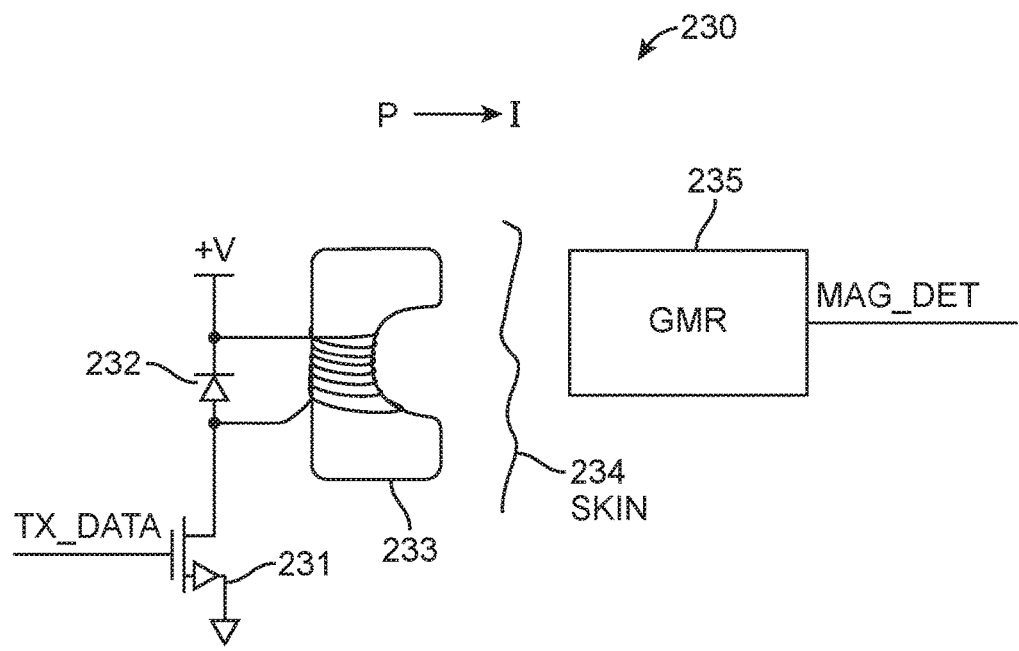
FIG. 26 shows a schematic of a programmer-to-implant telemetry scheme, according to many embodiments.
Figure 27:
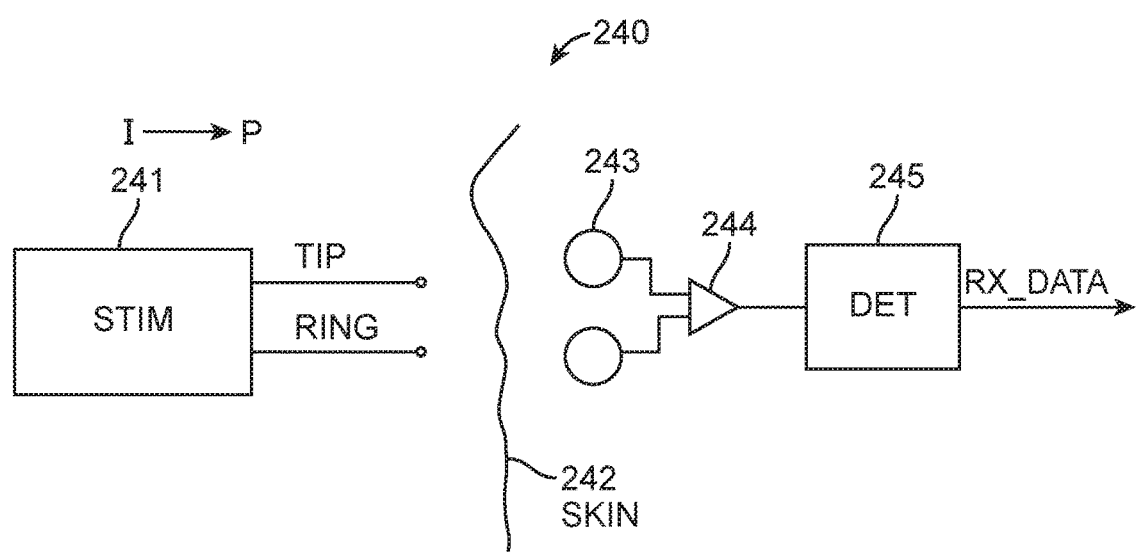
FIG. 27 shows a schematic of an implant-to-programmer telemetry scheme, according to many embodiments.
Figure 36:
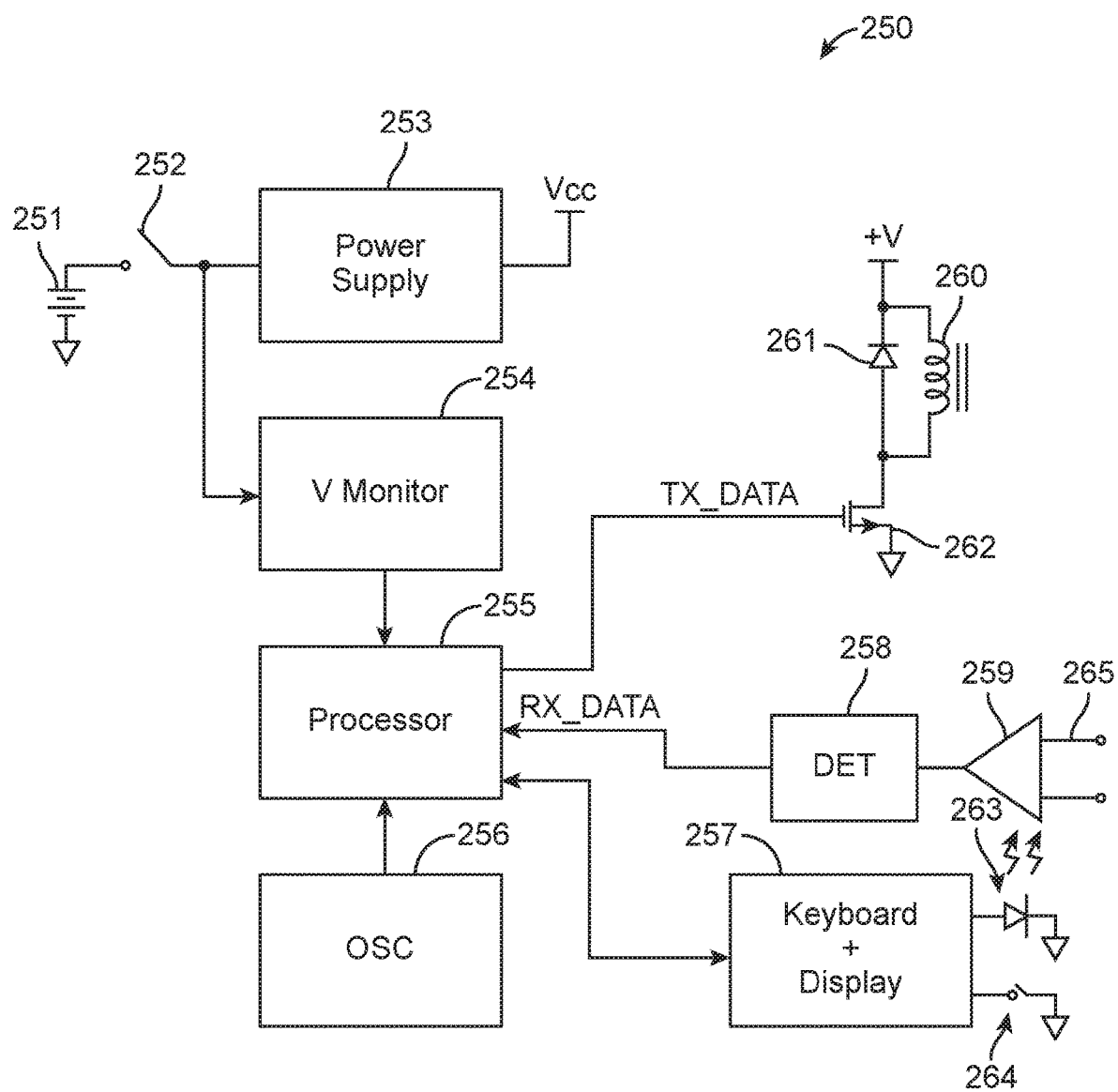
FIG. 36 shows a block diagram of an external programmer, according to many embodiments.

36—cell
37—ASIC
39—DC-blocking capacitor
40—hermetic feedthrough
41—TIP (cathodic stimulator output)
42—RING (anodic stimulator output)
43—RF coupling capacitor
FIG. 9
50—block diagram, miniature implanted neurostimulator ASIC
51—Q, V monitor
52—regulator
53—charge pump
54—processor
55—stimulator output
56—32 kHz oscillator
57—fast oscillator
58—implant telemetry
59—32 kHz external crystal
60—charge pump capacitor
61—charge pump capacitor
62—stimulator output
63—telemetry inductor
FIG. 10
65—limb wand
66—wand main housing
67—flexible strap
FIG. 11
70—limb wand
71—wand main housing
FIG. 12
75—torso programmer
76—programmer main housing
77—keyboard and display unit
78—flexible strap
FIG. 13
80—programmer with integrated PTNS stimulator
81—optional telemetry wand connection
82—TIP (cathodic stimulator output)
83—RING (anodic stimulator output)
84—keyboard and display unit
FIG. 14
85—block diagram of programmer with integrated PTNS stimulator
86—power supply
87—charge pump
88—V monitor
89—stimulator output
90—processor
91—oscillator
92—real time clock
93—implant telemetry
94—keyboard and display I/O
95—battery
96—on/off switch
97—charge pump capacitor
98—charge pump capacitor
99—DC-blocking capacitor
100—TIP connection
101—RING connection
102—telemetry inductor
103—display LED
104—key switch
FIG. 15
110—block diagram, limb wand
111—power supply
112—V monitor
113—processor
114—RF telemetry
115—implant telemetry
116—oscillator
117—keyboard and display I/O
118—battery
119—on/off switch
120—RF antenna
121—telemetry inductor
122—display LED
123—key switch
FIG. 16
125—low duty cycle stimulator state diagram
126—IDLE state
127—enable stimulator output state
128—transition occurring every week
129—transition occurring after 30 minutes
FIG. 17
130—low duty cycle stimulator with deferred therapy
131—IDLE state
132—enable stimulator output state
133—1-hour delay state
134—transition occurring every week
135—transition occurring after 30 minutes of stimulation
136—transition occurring after 1-hour delay
137—transition occurring after leg movement detected
FIG. 18
140—patient key fob
141—key fob housing
142—LED indicating key fob is active
143—LED indicating low battery status
144—key to activate key fob
FIG. 19
150—block diagram, patient key fob
151—power supply
152—V monitor
153—processor
154—RF telemetry
155—oscillator
156—display driver
157—battery
158—key switch
159—RF antenna
160—display LED
FIG. 20
165—smart phone key fob/programmer system via direct implant connection
166—human leg
167—miniature implanted neurostimulator
168—key fob app/programmer app running on smart phone
FIG. 21
170—smart phone programmer system via indirect implant connection
171—human leg
172—miniature implanted neurostimulator
173—programmer app running on smart phone
174—limb wand
FIG. 22
180—single incision surgical procedure
181—leg
182—incision
183—tunnel for generator
184—nerve
185—stimulation site FIG. 23
190—miniature implanted neurostimulator with alternative anchor
191—miniature implanted neurostimulator
192—anchor
193—flexible insulated lead wire
194—electrode assembly
FIG. 24
195—double incision surgical procedure
196—leg
197—secondary incision
198—primary incision
199—stimulation site
200—nerve
FIG. 25
210—miniature implanted neurostimulator with hybrid telemetry
211—cell
212—microprocessor
213—giant magnetoresistance sensor
214—voltage converter/charger
215—supply filter capacitor
216—inductor
217—flyback diode
218—stimulation tank capacitor
219—charge balancing resistor
220—input protection diode
221—charge balancing capacitor
222—stimulation pulse MOSFET
223—attenuator
224—attenuator
225—attenuator
226—32768 Hz crystal
227—hermetic feedthrough
228—RING connection
229—TIP connection
275—pull-up resistor
FIG. 26
230—programmer-to-implant telemetry scheme
231—programmer transmit switch
232—snubber diode
233—electromagnet
234—skin barrier
235—giant magnetoresistance sensor
FIG. 27
240—implant-to-programmer telemetry scheme
241—miniature implanted neurostimulator
242—skin barrier
243—programmer skin electrodes
244—amplifier/filter
245—detector
FIG. 36
250—block diagram, programmer
251—battery
252—on/off switch
253—power supply
254—voltage monitor
255—microprocessor
256—oscillator
257—keyboard and display I/O
258—detector
259—amplifier/filter
260—electromagnet
261—snubber diode
262—programmer transmit switch
263—display LED
264—key switch
265—skin electrodes I. Miniature Implanted Neurostimulator An exemplary miniature implanted neurostimulator is shown in FIG. 1. The generator portion may be packaged in a cylindrical form, typically 1.0 cc in volume or less and no more than 6 to 7 mm in diameter. The generator (1) may comprise a primary cell (3), typically lithium CFx chemistry, an electronics compartment (4), an anchor (2), and a header (5). The outer shell is typically made from medical grade titanium or stainless steel, and the enclosure is typically hermetic. The electronics compartment (4) may contain a hermetic feedthrough (not shown) to allow the cathodic (TIP) connection to pass through the header (5). The outer surface of the enclosure may be electrically connected to the anodic connection (RING). The header is typically made from medical grade epoxy, PEEK, or one or more other medical grade biocompatible polymers.

Flexible insulated lead wires (6) may connect the header (5) to the bipolar cuff electrode assembly (7). The flexible insulated lead wires are typically insulated with silicone rubber or polyurethane. The conductive wire material is typically MP35N and constructed as a multi-strand cable or multi-filar coil design for flexural strength. The bipolar cuff material is typically silicone rubber or polyurethane and the electrodes (8) and (9) are made from platinum or platinum iridium. The cuff electrode assembly encircles the nerve to stimulate. In this embodiment, the outer generator enclosure is coated with either silicone rubber, polyurethane, or Parylene. The outer enclosure (anode) may be electrically connected to the proximal cuff electrode (8) while the feedthrough connection (cathode) may connect to the distal cuff electrode (9). This configuration can prevent stimulating muscle adjacent to the outer enclosure.

The anchor feature (2) shown in FIGS. 1 through 4 is used to suture the stimulator to tissue or bone to prevent migration of the implanted neurostimulator.

In some embodiments, a unipolar cuff electrode assembly may be used as shown in FIG. 2. The cuff electrode assembly (10) may contain only one distal electrode (11) connected to the cathodic connection (TIP). This electrode may be connected via a flexible insulated lead wire (6) to the feedthrough (not shown) through an insulating header (5). The outer enclosure of the generator (1) is typically not coated and can therefore serve as the anodic electrode (RING).

In some embodiments, a unipolar rod electrode assembly (12) may be used as shown in FIG. 3. This electrode configuration may be placed adjacent to the intended nerve. The unipolar electrode assembly body is typically made from silicone rubber or polyurethane and the electrode made from platinum or platinum iridium. The generator (1) shown in FIG. 3 is similar to the generator (1) shown in FIG. 1. The outer enclosure may be un coated and can serve as the anodic (RING) electrode. The cathodic connection (TIP) may pass through the feedthrough (not shown), through an insulating header (5), may connect to the flexible insulated lead wire (6), and may ultimately connect to the distal electrode (13) by passing through an inductor (14). The inductor can serve as an RF trap for configurations where the telemetry scheme is RF rather than inductive. With RF telemetry, the RF energy may exit the electronic enclosure (4) via the same single feedthrough (not shown) used for the TIP connection. This can allow the proximal part of the lead wire to also act as an antenna while the inductor (14) prevents RF energy from reaching the distal electrode (13), preventing unintended current flow. If inductive telemetry is used, inductor (14) may not be required.

In the embodiments shown by FIGS. 1 to 3, the flexible insulated lead wire(s) are, for example, 2 to 4 cm in length, and can allow the distal electrode to be placed at the stimulated nerve site while allowing the generator to be located in comfortable position for the patient.

In some embodiment, a bipolar rod electrode assembly may be used as shown in FIG. 4. The electrode assembly (15) may contain two electrodes, a proximal electrode (16) connected to the anodic connection (RING) and a distal electrode (17) connected to the cathodic connection (TIP). The can may be coated and the flexible lead wire assembly may contain at least two insulated wires for the anodic and cathodic connections.

Although rod shaped electrodes are shown in FIGS. 3 and 4 for the electrode assembly, the shape of the electrode assembly may take on other forms to optimize one or more of the following: performance of the electrode, mechanical stability of the electrode, comfort, and ease of installation.

In the embodiments for the unipolar (FIG. 3) and bipolar (FIG. 4) rod electrode assembly, the preferred surgical procedure may create only one incision or puncture wound at the leg entry point and a blunt dissecting tool may be used to create a tunnel from the wound to the stimulation site. A pictorial diagram for this procedure is shown in FIG. 5. A small incision or puncture wound (22) may first be created in the leg. Then, a blunt dissection tool similar in diameter to the electrode diameter may be used to dissect a path for the electrode and flexible insulated wires (24). This tunnel may be made from the wound (22) to the intended stimulation site (21) adjacent to the nerve (26). Then, a larger dissection tool may be introduced into the same tunnel but only inserted a sufficient length to accommodate the miniature implanted neurostimulator body (23) as shown in FIG. 5. An example of the blunt dissection tool (30) is shown in FIG. 6. Each blunt dissection tool (30) may be made, for example, from a stainless steel rod (31) with the distal end shaped with a ball nose (radius of the tip equal to the ½ the diameter) and a plastic handle (32) on the other end. The rod may be, for example, malleable to create a curved path. It may also be preferred that the rod be visible under fluoroscopy to help position the distal electrode at the intended stimulation site, although ultrasound or other imaging is also foreseen. The incision site may then be closed.

An exemplary alternative surgical procedure that may require only one incision is shown in FIG. 22. A small incision or puncture wound (182) may first be created in the leg. The incision may exposes the stimulation site (185) allowing for any of the electrode assembly embodiments to be placed next to the nerve (184). Using a blunt dissection tool (30), a tunnel can be created for the miniature implanted neurostimulator (183). To prevent migration of the generator, a different anchoring method may be used for this alternative procedure. FIG. 23 shows a miniature implanted neurostimulator with an alternative anchor (190). The anchor (192) may be constructed from silicone rubber and can allow the generator to be placed in the tunnel (183) shown in FIG. 22. The anchor (192) of FIG. 23 can prevent device migration. The incision site can then be closed.

An exemplary alternate surgical procedure that may require two incisions is shown in FIG. 24. A primary incision or puncture wound (198) may first be created in the leg. The incision may expose the stimulation site (199) allowing for any of the electrode assembly embodiments to be placed next to the nerve (200). A secondary incision or puncture wound (197) may be created. Using a blunt dissection tool (30), a tunnel may be created between the two incision sites. The miniature implanted neurostimulator may then be inserted in the tunnel and the anchor mechanism (2) as shown in FIGS. 1 through 4 may be sutured in place via access from the secondary incision (197). Both incision sites may then be closed.

FIG. 7 shows a block diagram for the miniature implanted neurostimulator with inductive telemetry (35). The miniature implanted neurostimulator will typically be powered by a primary cell (36). This cell is typically lithium CFx but other chemistries are possible. A primary cell may be preferred due to the simplicity of the design, patient freedom from recharging, and high energy density. With a cell volume of approximately 0.75 cc, a cell capacity of approximately 230 mAH, for example, can be obtained with a lithium primary cell.

Connected to the cell (36) may be a mixed signal ASIC (37). This ASIC is typically designed and fabricated using standard CMOS processes and can contain both digital and analog circuitry. Connected to the ASIC may be a small inductor (38) to provide bidirectional inductive telemetry with a programmer. The stimulator output is also shown exiting the ASIC and may be connected to a DC-blocking capacitor (39). This capacitor can ensure that a charge-balanced waveform is applied to the stimulating electrode, thus avoiding electrode corrosion issues.

The DC-blocking capacitor (39) may connect through a hermetic feedthrough (40) to the TIP (41) connection (cathodic stimulator output). The hermetic feedthrough can protect the electronics compartment from the corrosive environment of the body. In preferred embodiments, a CFx cell (36) may be utilized. The cell housing may be made from titanium and can serve as the cell negative connection. As shown in FIG. 7, the cell negative connection may connect to the outer housing of the cell and can serve as the RING connection (anodic stimulator output) (42).

FIG. 8 shows a block diagram for the miniature implanted neurostimulator with RF telemetry (45). Rather than using inductive telemetry, the ASIC can provide RF telemetry. The RF output of the ASIC can be coupled via RF coupling capacitor (43) to the TIP electrode connection (41). RF energy can then be coupled to the flexible insulated lead wire (not shown) which can acts as an antenna. Alternatively, the electronics housing case can be made from ceramic (to allow the passage of RF), and a RF magnetic loop antenna could be realized within the electronics compartment. Other components such as a quartz crystal and additional passive components to generate and store the stimulator tank voltage may be provided as well but are not shown for clarity. Also not shown are the passive components, filter and crystal which may be provided to implement a RF transceiver. Also not shown are addition sensors such as a GMR sensor which may be provided to disable therapy and prevent interactions with MRI. Nor is there shown an accelerometer to detect leg movements when required to delay therapy. Which such aforementioned components are not shown, one or more of the components may be provided in the implanted miniature neurostimulators described above and herein.

An exemplary block diagram of the ASIC (50) is shown in FIG. 9. Power from a primary CFx cell can be supplied to the ASIC (50) through a charge and voltage monitor circuit (51). This circuit (51) can be responsible for monitoring the cell voltage and the total charge that has been withdrawn from the cell.

The output of the charge and voltage monitor circuit may feed the regulator (52) and charge pump (53). The regulator (52) may regulate the cell voltage, typically 3 V from a CFx cell to a lower voltage such as 1.2 V, to power the remaining blocks of the system. The regulator (52) typically performs this down-conversion using a capacitive divider (not shown for clarity) to keep power supply efficiency high.

The processor (54) may contains a microprocessor, typically an 8-bit or 16-bit core and may contain memory such as EEPROM, ROM, and static CMOS RAM provide storage for programs, programmable parameters, and diagnostic information. The processor may interface with the voltage and charge monitor circuit to provide a recommended replacement indicator for the physician. The processor may also control the charge pump circuit (53) and stimulation output circuit (55) and may communicate with the implant telemetry circuit (58). The processor may also interface to a 32K oscillator (56). This oscillator typically runs at 32768 Hz and may provide a clock reference for system functions. The oscillator may use an external quartz crystal (59) to provide accurate timing. The 32K oscillator may run continuously. A fast oscillator (57) may provide a clock to run the processor. This clock is usually 1 MHz or faster and may only be enabled when the processor is active. Bidirectional telemetry may be performed by an implant telemetry circuit (58). The implant telemetry circuit can typically interface with an inductor in the embodiments with inductive telemetry. In the embodiments with RF telemetry, a second ASIC reserved specifically for this function is typically required although a single ASIC design could be realized. With RF telemetry, a handful of passive components, a SAW filter, and an additional quartz crystal are typically required but are not shown for clarity.

The stimulation voltage required for the miniature implanted neurostimulator may be generated by the charge pump block (53). The charge pump may take the cell voltage and may generate a regulated voltage for stimulation. This regulated voltage may be higher or lower than the cell voltage. Typically, this regulation may be performed using a capacitive charge pump configuration known to those skilled in the art. Two charge pump capacitors are shown (60, 61) although more may be required. The output of the charge pump circuit may connect to the stimulator output circuit (55).

The stimulator output may generate either a constant voltage or constant current waveform for stimulation. The use of an external DC-blocking capacitor may ensure that the waveform is charge-balanced.

Other functions in the block diagram such as band-gap voltage source, current bias generators, and interfaces to other sensors such as a GMR sensor or accelerometer are not shown for clarity. The miniature implanted neurostimulator may be made possible because of the relatively low duty-cycle required for a therapeutic benefit. PTNS stimulation typically occurs for 30 minutes every week. This can translate to a duty-cycle of 0.5/168 or approximately 0.3%. Assuming a background current drain of 1 µA, a load resistance of 500Ω, a stimulation current of 10 mA, stimulation frequency of 20 Hz, stimulation pulse width of 200 µs and a cell capacity containing 230 mAH, for example, the miniature implanted neurostimulator will last more than 20 years.

Because of the low duty-cycle requirement, the longevity of the system may be very sensitive to the background current drain. The low background current drain may be due to the fact that only the Q, V monitor circuit (51), 32 K oscillator (56) circuit, and implant telemetry circuit (58) are typically always active. All other blocks can be disabled, consuming only static leakage current. It is not unreasonable to assume the following quiescent current drain for each block:

≤100 nA for the Q, V monitor circuit (51),
≤250 nA for the 32 K oscillator circuit (56),
≤500 nA for the implant telemetry circuit (58),
≤100 nA for static CMOS leakage at 37° C.

The total estimated background current may be 950 nA or less than 1 µA. It is not unreasonable to push these numbers down even further. With aggressive duty-cycling techniques the current drain for the Q, V monitor circuit and implant telemetry circuit could be reduced much further.

Another consideration for the miniature implanted neurostimulator may be the peak current taken from the cell. For a CFx cell of this size, the cell internal resistance is typically on the order of several hundred ohms. Therefore, the peak current from each of the functional blocks described in FIG. 9 should not cause the terminal voltage of the cell to drop below the useful minimum voltage. For example, if the lowest terminal voltage that could power the system is 2.0 V, then for a typical cell voltage of 3 V at beginning of service and a recommended replacement voltage of 2.5 V, the total peak current from the cell shall not exceed (2.5 V−2.0 V)/300 ohm=1.67 mA for all features in the device to work correctly at the recommended replacement time. The functional blocks which may require significant peak current from the cell are the following:

Charge pump. Delivering 10 mA at 20 Hz from a compliance of 5 V may require a capacitive multiplier circuit that doubles the cell voltage. During stimulation, the peak current from the cell may then be 10 mA*20 Hz*200 µs*2=80 µA, assuming 100% efficiency. Even at an efficiency of 20%, the peak current may only be 100 µA.

Implant telemetry. In the case of inductive telemetry, the peak current may be estimated to not exceed 200 µA during transmit. The receive current is typically not expected to exceed 50 µA. However, the use of MICS RF telemetry typically requires approximately 5 mA during either receive or transmit, thus exceeding the peak current requirements. To avoid this peak current, the Bluetooth Low Energy (BLE) protocol combined with an external decoupling capacitor across the cell terminal can be sufficient to reduce the cell peak current to an acceptable value. For example, a typical BLE peak current profile suitable for use in a miniature implanted neurostimulator is:

Pre-processing: 8 mA, 2 ms
TX/RX: 15 mA, 1 ms
Post-processing: 8 mA, 2 ms
Sleep: 0.1 µA, 20 s This profile would yield an average current of less than 1 µA and, when combined with a decoupling capacitor across the cell of 100 µF, would only result a voltage drop of [(8 mA*4 ms)+(15 mA*1 ms)]/100 µF=0.47 V, allowing RF communication at the recommended replacement time and still have the cell terminal voltage exceed the 2.0 V minimum.

Although the processor block consumes 50 to 100 µA peak when active, this peak current may be supplied from a regulated supply with its own decoupling capacitor. The firmware design and capacitor size can be optimized to ensure that voltage drop in the regulated supply is on the order of tens of millivolts.

FIG. 16 shows a state diagram for a low duty-cycle stimulator (125). Upon initialization, the stimulator can enter the IDLE state (126). After one week (128), the IDLE state can transition to the ENABLE STIM state (127). In this state, the miniature implanted neurostimulator can deliver pre-programmed neurostimulation therapy to the patient.

After 30 minutes expires (129), the stimulator can transition back to the IDLE state (126).

FIG. 17 shows a state diagram for a low duty-cycle stimulator with deferred therapy (130). In this embodiment, an accelerometer may be included in the miniature implanted neurostimulator to detect limb movement. Upon initialization, the stimulator may enter the IDLE state (131). After one week (134), the IDLE state may transition of the ENABLE STIM state (132). In this state, the miniature implanted neurostimulator can deliver pre-programmed neurostimulation therapy to the patient. If at any time during the therapy a leg movement is detected (137), the ENABLE STIM state can be exited to a 1 HR DELAY state. After 1 hour expires (136), simulation can be resumed by returning to the ENABLE STIM state (132). After 30 minutes of stimulation (135), the stimulator can transition back to IDLE state (131).

In some embodiments, neurostimulation therapy could be delivered when the patient is sleeping. The miniature implanted neurostimulator could contain a real-time clock that is programmed by the physician to deliver therapy at a time likely to coincide with the patient's sleep habits.

Although a miniature implanted neurostimulators that uses primary cell is described, a secondary (rechargeable) cell may be used in some embodiments.

Because of the low duty-cycle requirement of the therapy (0.3%), other technologies that allow for an implanted electrode to delivery therapy from an external power source may be provided. Magnetic, ultrasonic and RF technologies potentially allow for an even smaller implanted device to be placed on or near the sacral nerve for the purposes of treating urinary or bowel incontinence. The smaller implanted device may even be delivered via a percutaneous needle delivery system. In these cases, an external device may be present and held in reasonable proximity to the implanted device to allow the transfer of energy.

II. Programmer

An exemplary external programmer is shown in FIG. 10. FIG. 10 shows a cuff-like housing that can encircle the limb containing the miniature implanted neurostimulator. The limb wand (65) shown by FIG. 10 may comprise a wand main housing (66) and a flexible strap (67). The housing and strap may implement a toroidal coil configuration that encircles the limb, such that its magnetic field can align with the magnetic field of the implanted neurostimulator's telemetry inductor, which can also align with the long axis of the neurostimulator. The strap (67) may contain ferrite material to form a highly permeable magnetic path completely encircling a limb. Aligning the magnetic fields of both the implanted neurostimulator and limb wand (65) can provide optimal coupling and can result in more reliable communication without the troublesome need to position the wand as in inductive telemetry systems.

As shown in FIG. 11, an exemplary limb wand (70) may completely encircle the patient's leg. The programmer's telemetry coil (not shown), contained inside the housing (71), can completely encircle the leg and can avoid the flexible strap. The limb wand (70) must be placed over the patient's foot and ankle before it is positioned along the leg and in proximity to the miniature implanted neurostimulator.

The limb wands (65, 70) shown in FIG. 10 or 11 may contain the inductive communications circuitry needed to communicate with the miniature implanted neurostimulator and may also contain additional RF circuitry to relay the bi-directional communication with the implant to a smart phone, desktop, laptop or tablet computer via Bluetooth low energy or equivalent. The limb wand can be completely self-contained and may act as a relay such that an ordinary smart phone communicates with the inductive-telemetry-based miniature implanted neurostimulator via the limb wand.

The block diagram (110) for such relay embodiments is shown in FIG. 15. The limb wand may contain a battery (118) connected via an on/off switch (119) to a power supply (111). A processor (113) may contain an 8, 16, or 32-bit microprocessor and memory such as EEPROM, ROM, and static CMOS RAM to provide storage for programs. An oscillator (116) is may be connected to the processor (113) to provide a system clock.

The processor (113) may communicate with an implant telemetry block (115) containing circuitry to communicate with the miniature implanted neurostimulator. The output of the implant telemetry block may connect to an inductor (121). The processor (113) may also communicate with an RF telemetry block (114) to communicate with a smart phone (114). The output of the RF telemetry block may connect to an RF antenna (120). The antenna may be an electric field or magnetic field antenna and the RF telemetry system may contain more than one antenna for the purpose of implementing diversity.

The processor (113) may also communicate with a keyboard and display block (117) to provide I/O. An example of one display LED (122) and one key input (123) is shown in FIG. 15 although more may be provided. Although an LED implementation is shown in FIG. 13, LCD or other technology could also be used.

The processor (113) in the limb wand may also connect to monitor the battery voltage (112) and can provide an indicator to the physician that the internal battery needs to be replaced in the case of primary cells, or to indicate that the internal battery needs recharging in the case of secondary cells.

An audible feedback transducer may be anticipated for the programmer but the implementation is not shown.

FIG. 21 shows an exemplary smartphone programmer system (170) working with the patient's leg (171). The system (170) may comprise the miniature implanted neurostimulator (172), the limb wand (174), and the smartphone programmer (173). The smartphone (173) may be used as the programmer, and communications with an inductive based miniature implanted neurostimulator can occur through the limb wand (174) that can act as a relay to allow the RF based smartphone (173) to communicate with the inductive based miniature implanted neurostimulator.

FIG. 12 shows another exemplary external programmer (75). Here, the key input and display output (77) may be integrated into the torso programmer (75). The programmer main housing (76) is shown along with the flexible strap (78). Just as in the limb wand, the torso programmer (75) can allow the alignment of the programmer and miniature implanted neurostimulator for more reliable communication when an inductive telemetry scheme is used.

FIG. 13 shows another exemplary external programmer (80). Here, the programmer (80) may contain electronics to receive input and display output (84) such that the user can program and interrogate the miniature implanted neurostimulator. Additionally, the programmer may incorporate a neurostimulator generator for delivering PTNS therapy during an evaluation phase that may be required before a patient is implanted with a device. The programmer (80) may communicate with the implant via RF telemetry such as that shown and described above with reference to FIG. 3 or 4, or the programmer may connect to a limb wand such as that shown and described above with reference to FIG. 10 via RF or a cable (81) (connection not shown in FIG. 10).

This programmer/neurostimulator (80) can provide a TIP (82) and RING (83) connection that may be connected to a transcutaneous needle and adhesive patch electrode respectively for the purpose of demonstrating the efficacy of the neurostimulation therapy.

The block diagram for a programmer with integrated PTNS generator (85) is shown in FIG. 14. The programmer (85) may contains a battery (95) connected via an on/off switch (96) to a power supply (86) to provide a regulated voltage. A processor (90) may contain an 8, 16 or 32-bit microprocessor and memory such as EEPROM, ROM and static CMOS RAM to provide storage for programs. An oscillator (91) can be used to provide a system clock. A real-time clock (92) may also be provided to allow real-time events to be programmed in the miniature implanted neurostimulator.

The processor (90) may communicate with an implant telemetry block (93) containing circuitry to communicate with the miniature implanted neurostimulator. This implant telemetry block may connect to an inductor for communication with an inductive based miniature implanted neurostimulator. In the case of an RF based miniature implanted neurostimulator, the implant telemetry circuitry may contain an RF transceiver and may connect to one or more RF antennas. Alternatively, the implant telemetry circuitry may provide for a hardwire connection to the limb wand.

The processor (90) may also control the charge pump (87) and stimulator output circuitry (89). The charge pump may take the regulated voltage from the power supply (86) and may generate a regulated voltage used for stimulation. Typically, this regulation may be performed using a capacitive charge pump configuration known to those skilled in the art. Two charge pump capacitors are shown (97, 98), although more may be required. The output of the charge pump circuit may connect to the stimulator output circuit (89).

The processor (90) may also control the stimulation output circuitry (89). The stimulator output may generate either a constant voltage or constant current waveform for stimulation. The use of a DC-blocking capacitor (99) can ensure that the waveform is charge-balanced.

The processor may monitor the battery voltage (88) to provide an indicator to the physician that the internal battery needs to be replaced in the case of primary cells or indicate that the internal battery needs recharging in the case of secondary cells. The processor (90) may also communicate with the keyboard and display circuitry (94) to provide I/O. An example of one display LED (103) and one key input (104) is shown in FIG. 14, although more may be provided. Although an LED implementation is shown in FIG. 14, LCD or other technology could also be used.

III. Key Fob

An RF-based miniature implanted neurostimulator can also be activated by a patient operated key fob (140) as shown in FIG. 18. The key fob (140) may comprise a housing (141), a key (144) that the patient presses to activate the key fob action, an LED to indicate that the key fob is active (142), and an LED to indicate when the key fob battery must be replaced (143). The LED indicating that the key fob is active (142) may be enabled when the key (144) is pressed, or may be enabled only when the key (144) is pressed and the key fob has confirmed that the miniature implanted neurostimulator has received the key fob command. The key fob may choose to distinguish between a single click, delayed hold, and a double click to send unique commands, or additional keys may be included on the key fob for unique commands.

Activation of the key fob by the patient may result in a pre-programmed command to be executed by the miniature implanted neurostimulation. Commands may be selected and modified by the physician using the programmer. More than one command may be available to be executed by the miniature implanted neurostimulator.

An exemplary block diagram for the patient key fob (140) is shown in FIG. 19. The key fob (140) may contain a battery (157) connected via an on/off switch (158) to a power supply (151) to provide a regulated voltage. A processor (153) may contain an 8, 16, or 32-bit microprocessor and memory such as EEPROM, ROM and static CMOS RAM to provide storage for programs. An oscillator (155) may be used to provide a system clock.

The processor (153) may communicate with an RF telemetry circuit (154) containing circuitry to communicate with an RF based miniature implanted neurostimulator. The RF telemetry block (154) may connect to an RF antenna (159).

The processor (153) may monitor the battery voltage (152) to provide an indicator to the user than the internal battery needs to be replaced in the case or primary cells or indicate that the internal battery needs recharging in the case of secondary cells. The processor (153) can also communicate with a display driver (156) to illuminate one or more LEDs to indicate low-battery or that the transmitter is active. Only one LED (160) is shown in FIG. 19; however, more than one may be implemented.

An audible feedback transducer may be provided for the key fob, but the implementation is not shown. In other embodiments, the dedicated key fob is replaced by a smartphone. In this case, the RF standard used by the smartphone and the miniature implanted neurostimulator may be compatible such as with BLE.

The smart phone/key fob system is shown in FIG. 20. The human leg (166) and miniature implanted neurostimulator (167) and the patient activated key fob or smart phone (168) are illustrated. Either the key fob or smartphone can communicate directly with the miniature implanted neurostimulator via RF.

IV. Hybrid Telemetry

As discussed above and herein, both RF and inductive telemetry schemes can be provided for the miniature implanted neurostimulator. In some embodiments, a hybrid scheme can be provided. The hybrid scheme can provide for programmer-to-implant (P-to-I) communication to occur via magnetic fields while implant-to-programmer (I-to-P) communication occurs via conductive telemetry. An advantage of such a system is that bidirectional telemetry can be performed using a minimum number of components in the implant. For example, the I-to-P communications channel may start with a transmitter in the implant that reuses the same hardware and electrodes as used for neurostimulation and the P-to-I communications channel implant receiver can use a GMR sensor that occupies an area of only 1.1 mm by 1.1 mm. This configuration can provide a simple and compact embodiment for bidirectional telemetry in an implanted neurostimulator.

An exemplary block diagram for the miniature implanted neurostimulator that supports this hybrid telemetry scheme is shown in FIG. 25. The cell (211) can power a microprocessor (212). Internal to the microprocessor is typically a high frequency oscillator, typically 0.5 to 8 MHz, to clock the internal core; however, an external 32K (32768 Hz) crystal (226) is shown, which may provide a real-time clock to determine stimulation pulse width and periods accurately. A voltage converter/charger (214) is shown, which may convert the cell voltage to a higher voltage for stimulation. The charger (214) is typically a boost regulator that uses an inductor (216) to store energy when the SW terminal of (214) is connected to ground. The voltage can be boosted when the SW terminal is released from ground and the stored energy is released from the inductor and passes through the flyback diode (217), transferring the energy to the stimulation tank capacitor (218). The microprocessor (212) can provide a digital-to-analog converter (DAC) connected to the signal, TARGET. The resistor network (223, 224 and 225) may form an attenuator network providing a feedback signal (FB) to the charger. The feedback signal may typically be compared to an internal reference voltage to regulate the voltage on the stimulation tank capacitor (218). By varying the DAC voltage on TARGET, the stimulation voltage can typically be set anywhere from 10 V to the cell voltage minus a diode drop. The microprocessor (212) can disable the voltage converter/charger to conserve energy by de-asserting the EN signal. The miniature implanted neurostimulator may provide stimulation by asserting the STIM signal from the microprocessor and closing the stimulation pulse MOSFET switch (222). When the switch is closed, a monophasic truncated exponential pulse can be applied between the TIP (229) and RING (228) terminals. The stimulation pulse current can flow through a charge balancing capacitor (221) that accumulates charge during the stimulation pulse. Following stimulation, the charge stored on the charge balancing capacitor can be discharged back through the RING and TIP via resistor (219). Diode (220) can provide protection against electrosurgery and other external influences that could affect the integrity of the system. A giant magnetoresistance sensor (GMR) may connect to the microprocessor providing a signal, MAG_DET_B, when an external magnetic field is detected. The sensor can be enabled by asserting the GMR_EN signal. Pull-up resistor (275) may keep the open-collector output of the sensor de-asserted.

I-to-P communication can occur via conducted communications using the identical circuitry to create stimulation pulses between the RING and TIP electrodes. Information can be sent by the implantable stimulator by applying short (typically 10 to 15 μs) pulses between the TIP and RING terminals such that the stimulation pulses are sub-threshold and have no therapeutic value. The electric field generated between the TIP and RING terminals can then be detected on the skin surface by the programmer and decoded for use in an I-to-P communication channel. In this example, the implant has two electrodes, but alternative embodiments with more than two electrodes could also be used.

FIG. 27 illustrates I-to-P communication. The miniature implanted neurostimulator (241) is shown with TIP and RING electrode connections. The skin barrier (242) is shown to highlight that the programmer skin electrodes can pick-up a far-field signal generated by the TIP and RING electrodes, and that I-to-P communications can occur wirelessly from implant to programmer, albeit with the use of electrodes placed on the surface of the skin. FIG. 27 shows an amplifier/filter (244) connected to the programmer skin electrodes. In this example, the programmer uses two skin electrodes, but alternative embodiments with more than two skin electrodes could also be used. For example, the programmer could automatically select the electrode configuration that provides the optimal signal strength or signal to noise ratio.

The output of the amplifier/filter may connect to a detector (245), whose output is a decoded signal, RX_DATA. The detector could be a simple comparator whose output is asserted when the signal exceeds a predetermined threshold. FIG. 27 shows a simplified example of the basic signal processing that can be used to decode the I-to-P signal. This processing could be performed using analog circuitry, digital circuitry, software, or a combination thereof. The amplifier/filter (244) can also contain input protection circuitry (not shown).

Stimulation at approximately 2.5 V by the implant will result in a millivolt level signal appearing on the skin surface. Therefore, a gain of approximately 3000 may be required for the amplification shown by FIG. 27. Although more sophisticated filter approaches can be applied either in the analog or digital domains, a simple band-pass filter, with a low-pass corner set to acquire 90% of the pulse amplitude within the first 10% of the pulse duration, assuming a 10 μs is pulse, can give a low-pass corner of 300 kHz. The high-pass corner may be set with the longer 15 μs pulse such that the pulse sags only ⅓rd, resulting in a high-pass corner of 10 kHz.

P-to-I communication can occur via magnetic fields generated by the programmer. Modulation of magnetic fields by the programmer, for example, by the use of an electromagnet, may be detected in the implantable stimulator by the GMR sensor, creating a P-to-I communications channel. FIG. 26 illustrates P-to-I communication. The programmer hardware may generate a data signal, TX_DATA, which may enable a programmer transmit switch (231) and may energize an electromagnetic (233). Flyback diode (232) may act as a snubber, protecting the programmer switch (231). The skin barrier (242) is shown in FIG. 26 to highlight that the external electromagnet and GMR sensor may be separated by a short distance, typically 2 to 10 cm, and that P-to-I communication may occur wirelessly from programmer to implant. FIG. 26 also identifies the GMR sensor located in the miniature implantable neurostimulator. The output of the GMR sensor, MAG_DET_B, can convey the information sent by the signal TX_DATA.

In an example, the electromagnet may comprise a soft-iron core solenoid, where the cross-section of the core is 0.8 $cm^2$ in diameter, 14 cm in length with an air gap of 4 cm. With a relative permeability of iron equal to 200, the reluctance of the core may be approximately 6.1 (1/μH) and the reluctance of the air gap may be approximately 354 (1/μH). For a coil with 300 turns on the iron core with a peak current of 3 A, the resulting magnetomotive force, F, may be equal to 900 Wb/H. The total flux, φ, can be given by F/R, where R is the reluctance of the iron core and the air gap combined. The total flux may be 2.5 μWb. The flux density in air may be given by the relationship, B=φ/RAIR, which may give a flux density in air of approximately 28 mT. The GMR sensor used may be, for example, a BD927-14E, manufactured by NVE Corporation, Eden Prairie Minn. This sensor has a typical operating point of 15 Oersteds, which corresponds to 1.5 mT. The flux density across the air gap of the electromagnet may be sufficient to trigger the GMR, even at the location of the implant, which is off-axis with respect to the magnet's air gap.

Figure 28:
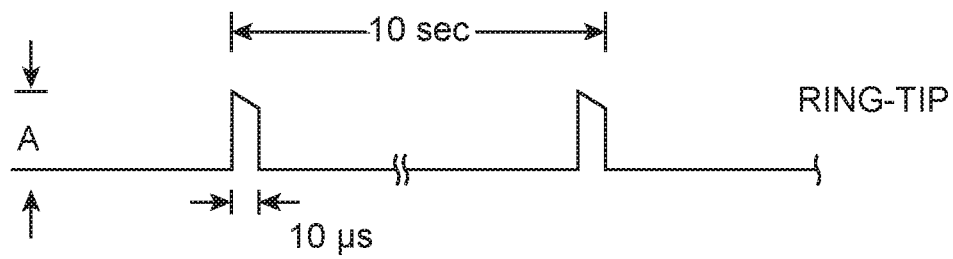
FIG. 28 shows a graph of implant marker synchronization pulses when there no link established, according to many embodiments.

The sensor may have a typical quiescent current drain at 2.4 V equal to 75 μA. To conserve energy, the microprocessor (212) in the FIG. 25 block diagram may enable the sensor only at infrequent intervals. However, since the GMR sensor may be enabled for a relatively short period, the programmer may not know when the GMR sensor is active. To solve this, the implant may provide a synchronization pulse to the programmer, letting the programmer know when to enable the electromagnet and send information back to the programmer. This process is first demonstrated in FIG. 28. Here, the miniature implantable neurostimulator can send a subthreshold pulse between the RING and TIP electrodes with a pulse width of 10 µs. This short pulse may be sent every 10 seconds by the implant during periods that are otherwise inactive. The amplitude of the pulse is typically the cell voltage minus one diode drop. The implant can enable the GMR sensor following each short pulse, looking for confirmation that a programmer is present.

If no programmer is present, the implant may simply continue sending short pulses every 10 seconds between the RING and TIP. The energy consumed during this short pulse and the energy consumed by enabling the GMR sensor relatively infrequently may be negligible.

Figure 29:
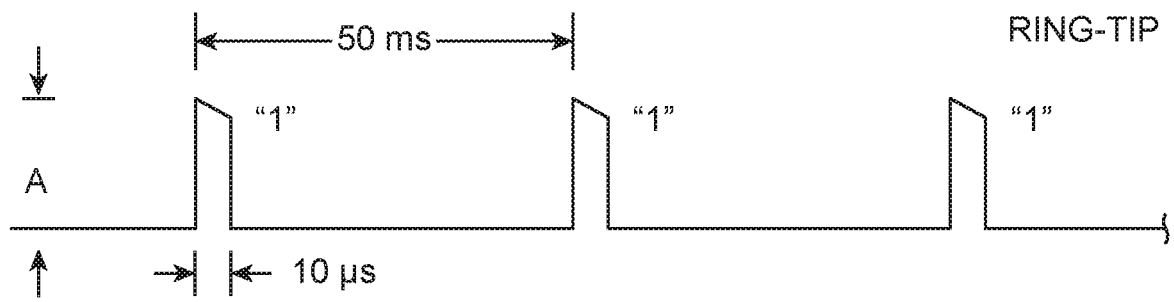
FIG. 29 shows a graph of implant marker synchronization pulses when there is a link established, according to many embodiments.

However, when a programmer is present, e.g., when skin electrodes are connected to the limb near the implant site and the programmer wand is positioned close to the implant, the programmer may detect the short pulses. Therefore, the programmer can enable the programmer's electromagnet when the implant's GMR sensor is active. In this way, a link can be established between the programmer and implant. When the implant detects a magnetic pulse using the GMR sensor, the implant can send short pulses between the RING and TIP every 50 ms. In this way, data throughput in both directions can be increased. FIG. 29 shows the miniature implanted neurostimulator sending short pulses (10 µs) between RING and TIP but at a rate of 20 Hz. The implant may also enable the GMR sensor following each short pulse to look for data being sent from the programmer via an electromagnet.

Communication can also occur while the miniature implanted neurostimulator is delivering therapy. An example of this is shown in FIG. 30. The RING TIP signal may show short 10 µs pulses occurring every 50 ms. After each short pulse, a longer, therapeutic stimulation pulse with a duration of 200 µs may occur. The programmer can distinguish the short, subthreshold pulses from the longer therapeutic pulses.

Figure 31:
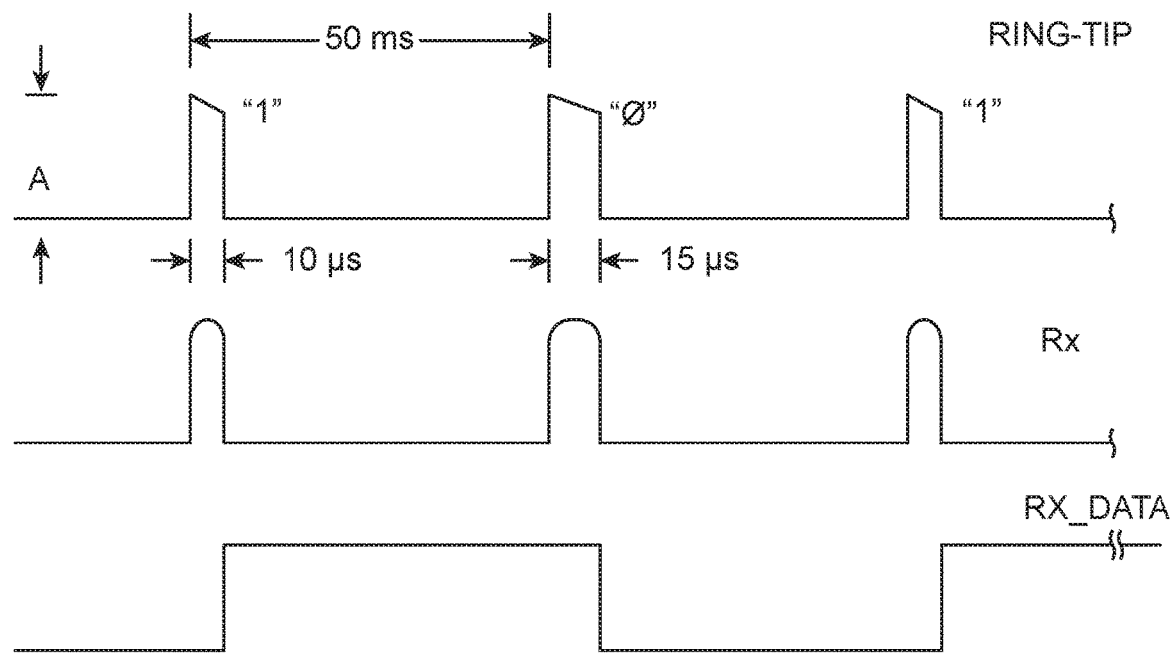
FIG. 31 shows a graph of exemplary implant-to-programmer communication data, according to many embodiments.

An example of I-to-P data communication is shown in FIG. 31. FIG. 31 shows a data "1" identified as a short 10 µs pulse, while a data "0" is identified as a longer, 15 µs, but still subthreshold, pulse absent by the implant. The programmer may receive this signal via two or more skin electrodes and amplifies and filters this signal. The received signal before detection is shown as the signal RX. The detector and associated processing circuitry and/or software can distinguish short (10 µs) pulses from long (15 µs) pulses and outputs a "1" following each short pulse and a "0" following a long pulse. The RX_DATA signal in FIG. 31 illustrates this.

Figure 32:
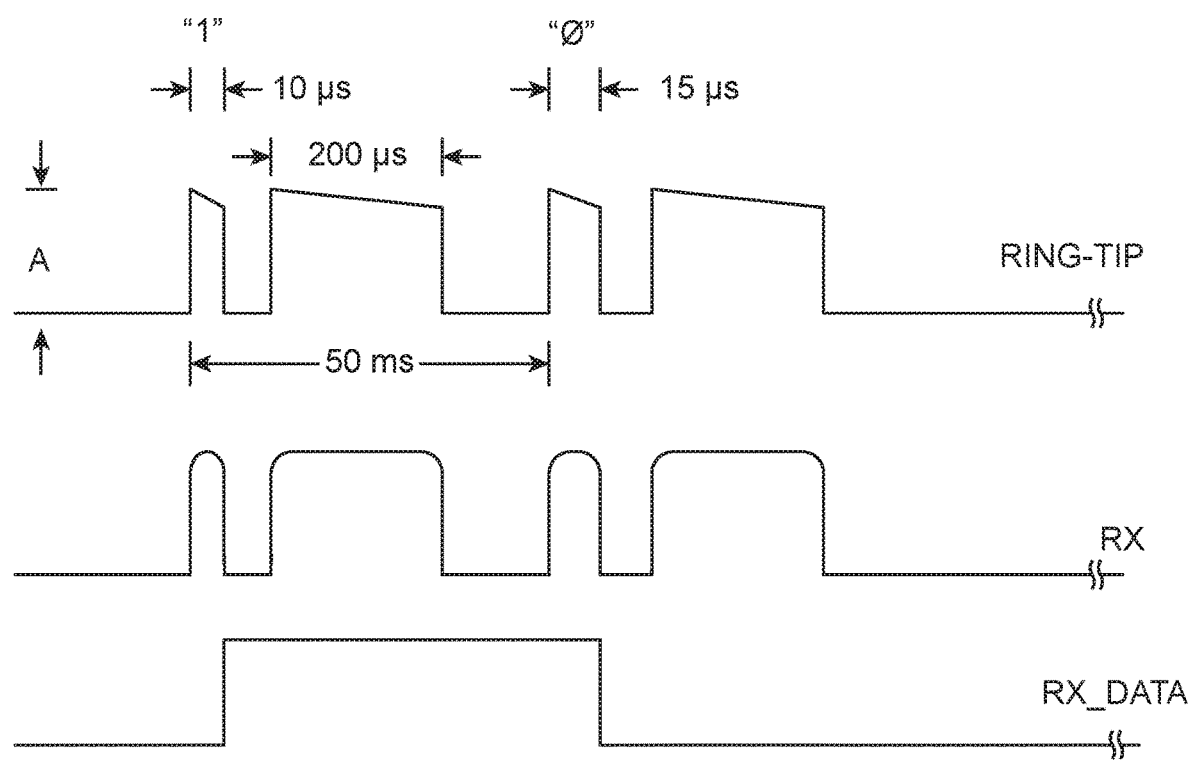
FIG. 32 shows a graph of exemplary implant-to-programmer communication data, according to many embodiments.

An example of I-to-P data communication during neurostimulation therapy is shown in FIG. 32. FIG. 32 shows a data "1" identified as a short 10 µs pulse, followed by a 200 µs therapeutic pulse. After the first 50 ms, it shows a data "0" identified as a longer 15 µs pulse again followed by a 200 µs pulse. After amplification and filtering, the programmer may provide the RX signal as a faithful reproduction of the implant-generated waveform. The detector and associated processing circuitry and/or software may distinguish short (10 µs) from long (15 µs) pulses and may be refractory to even longer (200 µs) therapeutic pulses. The RX_DATA signal in FIG. 32 illustrates this concept.

Figure 33:
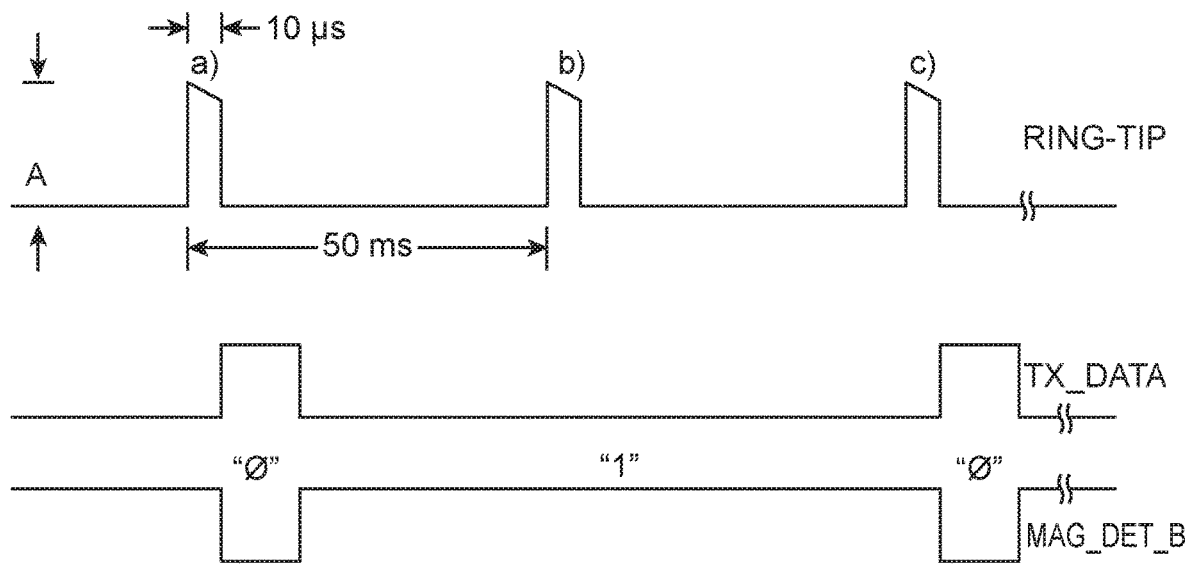
FIG. 33 shows a graph of exemplary programmer-to-implant data, according to many embodiments.

An example of P-to-I data communication is shown in FIG. 33. FIG. 33 shows three short (10 µs) synchronization pulses send by the implant. When the implant is expecting to receive data, the GMR sensor may be activated following each synchronization pulse. The programmer can then send data at the correct time for detection by the implant. An example of this is shown by the signal TX_DATA in FIG. 33. The programmer may send a data "0" following the first pulse (a) by asserting TX_DATA, may send a data "1" by not asserting TX_DATA following the second pulse (b), and may send another data "0" following the third pulse (c) by asserting TX_DATA. The received electromagnetic signal, MAG_DET is shown. The microprocessor may acknowledge a data "0" following the assertion of the MAG_DET_B signal after the first pulse. Since no assertion of MAG_DET_B occurred following the second pulse, the microprocessor may interpret this as a data "1" and so on.

Figure 34:
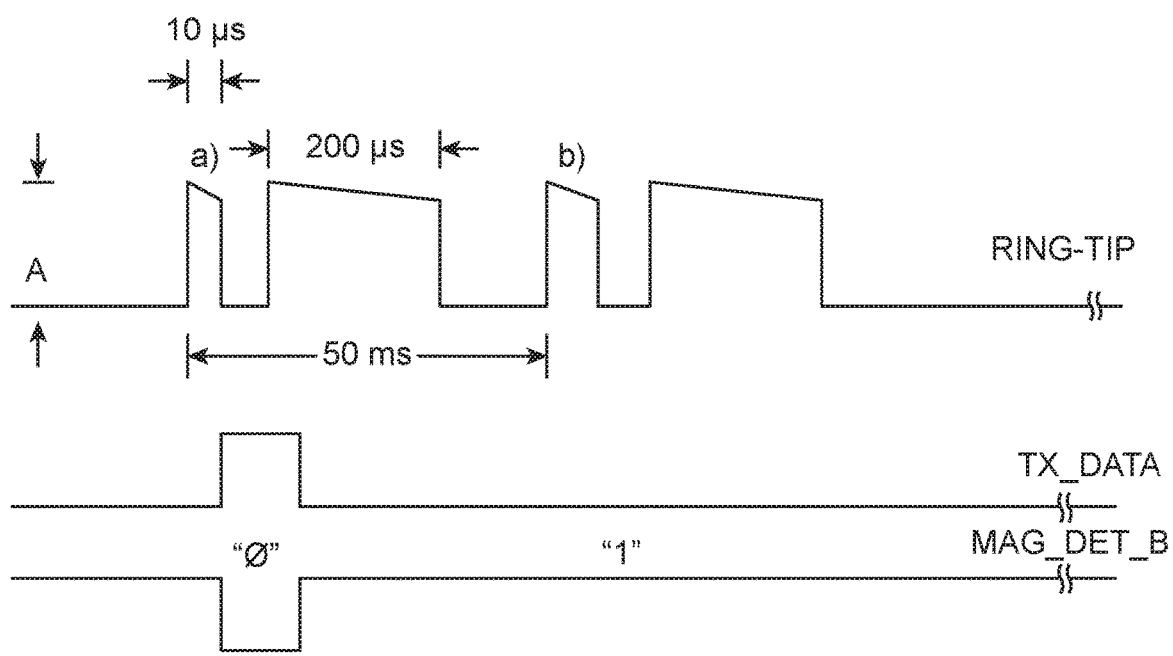
FIG. 34 shows a graph of programmer-to-implant data example during stimulation, according to many embodiments.

An example of P-to-I data communication during neurostimulation therapy is shown in FIG. 34. FIG. 34 shows a short (10 µs) synchronization pulse followed by a 200 µs therapeutic pulse. After 50 ms, it shows another short synchronization pulse followed by another therapeutic pulse. After the first synchronization pulse, the programmer may send a data "0" by asserting TX_DATA. After the second synchronization pulse, the programmer may send a data "1" by not asserting TX_DATA. The received electromagnetic signal, MAG_DET_B is shown. Since the programmer's detector and associated processing circuitry and/or software may distinguish short synchronization pulses from long therapeutic pulses, the programmer may assert TX_DATA following each synchronization pulse when a data "0" is required and may not assert TX_DATA following synchronization pulses when a data "1" is required.

In this example, only one symbol is sent per bit. Therefore, the symbol rate and data rate may be equal and set to 20 Hz. This data rate was chosen to coincide with the stimulation frequency, greatly simplifying the transmission and reception of data. However, the number of symbols per bit could be increased with different modulation schemes and the rate could be increased beyond the stimulation frequency with added complexity.

An exemplary method to decode the data streams received by the implant and by the programmer may be to format the data in non-return-to-zero (NRZ) serial format and use a serial universal asynchronous receiver/transmitter (UART). An example of this is shown in FIG. 35. When used with a serial UART, NRZ data format follows the convention of sending a start bit, followed typically by 8 data bits, starting from LSB (D0) to MSB (D7), followed by a at least one stop bit. Often the format may provide an additional parity bit. This example may use one start bit, one stop bit and no parity bit, as seen by trace a) in FIG. 33. In the first example, I-to-P data communication is shown in traces b and c. Trace b) shows short (10 µs) pulses to indicate a data "1" and long (15 µs) pulses to indicate a data "0". Typically, a data "1" would be sent prior to the transmission of the start bit. The first occurrence of a data "0" (long, 15 µs pulse) may indicate the start bit. The programmer may receive and interpret the implant signal by generating RX_DATA as seen in trace c). The data byte received by the programmer may be decoded as 0xA5. In the second example, P-to-I data communication is shown in traces d), e), and f). Trace d) shows short (10 µs) synchronization pulses send by the implant. Trace e) shows TX_DATA, where data "0s" are occasionally sent following a synchronization pulse. In this example, a data "0" is sent following the synchronization pulses for the start bit, bits D1, D3, D4, and D6. The received electromagnetic signal may be captured by the GMR detector and shown in trace f, signal MAG_DET_B. The data byte received by the implant may be decoded as 0xA5.

This example describes half-duplex communication, where I-to-P or P-to-I communication may be mutually exclusive. Because the communication methods used in the physical layer may be independent, electromagnetic in the case of P-to-I and conducted in the case of I-to-P, full-duplex communication can be easily achieved. The programmer may be able to synchronize not only to short (10 μs) pulses identified as a data "1" for I to P communication but also to synchronize to long (15 μs) pulsed identified as a data "0" for I to P communication.

This example describes only the physical layer and a rudimentary data link layer typical of an ISO network protocol. The remaining layers are contemplated but not described here. Typically, an end-to-end protocol is implemented, complete with checks to ensure data integrity and enhancements to provide communications in the presence of noise.

Embodiments provide for a programmer implemented in various physical embodiments. In some embodiments, all the elements required for programmer operation are contained in a single housing. In some embodiments, some of the elements are contained in a first housing and other elements are contained in a second housing intended for placement near the implant, called a "wand". In some embodiments, the two housings may be connected by a cable or by wireless means. In some embodiments, a third housing contains a power supply. For convenience the following description refers to the ensemble of elements as a "programmer/wand".

The programmer/wand block diagram is shown in FIG. 36. In this example, the programmer/wand comprises a battery (251) connected via an on/off switch (252) to a power supply (253). A processor (255) comprises an 8-bit, 16 or 32-bit microprocessor and memory such as EEPROM, ROM and static CMOS RAM to provide storage for programs. An oscillator (256) is shown connected to the processor to provide a system clock.

The processor may send information to the implant by asserting TX_DATA and driving the electromagnetic assembly composed of switch (262), electromagnet (260), and snubber diode (261). The microprocessor may receive information from the implant by detecting conducted telemetry signals on the skin electrodes (265) connected to the amplifier/filter (259), detecting these signals (258) and decoding the RX_DATA signal.

The processor may also communicate with a keyboard and display block (257) to provide user input/output (I/O). An example of one output LED (263) and one input key (264) is shown although more may be provided. Although an LED implementation is shown, LCD or other technology could also be used.

The programmer/wand also may not contain a keyboard and display unit but rather provide a USB connection or Bluetooth connection to a tablet where the keyboard and display unit may reside.

The processor in the limb wand may also connect to monitor the battery voltage (254) and may provide an indicator to the physician that the internal battery needs to be replaced in the case of primary cells, or to indicate that the internal battery needs recharging in the case of secondary cells.

An audible feedback transducer may be provided for the programmer.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the present disclosure described herein may be employed in practicing the inventions of the present disclosure. It is intended that the following claims define the scope of the invention and that methods and structures within the scope of these claims and their equivalents be covered thereby.

What is claimed is:

1. An implantable device for permanent implantation in a body of a subject for long-term use to stimulate nerve or other tissue, the device comprising:
    an enclosure configured to be implanted in a body of a subject;
    a battery disposed within the enclosure;
    circuitry disposed within the enclosure and coupled to the battery, the circuitry being configured to generate a stimulation signal with a duty cycle of between 0.1% and 2.5% and a total average current drain from the battery of between 0.1 μA and 5 μA, the total average current drain comprising a background current, plus a stimulation current weighted by the duty cycle, wherein the battery provides power to the circuitry to generate the stimulation signal;
    an electrode assembly coupled to the enclosure and the circuitry, the electrode assembly configured to direct the generated stimulation signal to the nerve or other tissue of the subject; and
    a lead coupling the electrode assembly to the enclosure and separating at least a portion of the electrode assembly from the enclosure.

2. The implantable device of claim 1, wherein the useful life of the implantable device is in a range of between 5 and 35 years, 6 and 34 years, 7 and 33 years, 8 and 32 years, 9 and 31 years, 10 and 30 years, 11 and 29 years, 12 and 28 years, 13 and 27 years, 14 and 26 years, 15 and 25 years, 16 and 24 years, 17 and 23 years, 18 and 22 years, or 19 and 21 years.

3. The implantable device of claim 1, wherein the duty cycle of the stimulation signal is in a range of between 2.4% and 0.1%, 2.3% and 0.1%, 2.2% and 0.1%, 2.1% and 0.1%, 2.0% and 0.1%, 1.9% and 0.1%, 1.8% and 0.1%, 1.7% and 0.1%, 1.6% and 0.1%, 1.5% and 0.1%, 1.4% and 0.1%, 1.3% and 0.1%, 1.2% and 0.1%, 1.1% and 0.1%, 1.0% and 0.1%, 0.9% and 0.1%, 0.8% and 0.1%, 0.7% and 0.1%, 0.6% and 0.1%, 0.5% and 0.1%, 0.4% and 0.1%, 0.3% and 0.1%, or 0.2% and 0.1%.

4. The implantable device of claim 1, wherein the circuitry is configured to generate the stimulation signal for 30 minutes once a week.

5. The implantable device of claim 1, wherein the background current is in a range of between 4.5 μA and 0.10 μA, 4.0 μA and 0.10 μA, 3.5 μA and 0.10 μA, 3.0 μA and 0.10 μA, 2.5 μA and 0.10 μA, 2.0 μA and 0.10 μA, 1.5 μA and 0.10 μA, 1.0 μA and 0.10 μA, 0.9 μA and 0.10 μA, 0.8 μA and 0.10 μA, 0.7 μA and 0.10 μA, 0.6 μA and 0.10 μA, 0.5 μA and 0.10 μA, 0.4 μA and 0.10 μA, 0.3 μA and 0.10 μA, or 0.2 μA and 0.1 μA.

6. The implantable device of claim 1, wherein the generated stimulation signal has a stimulation pulse current in a range of between 19 mA and 1 mA, 18 mA and 2 mA, 17 mA and 3 mA, 16 mA and 4 mA, 15 mA and 5 mA, 14 mA and 6 mA, 13 mA and 7 mA, 12 mA and 8 mA, or 11 mA and 9 mA.

7. The implantable device of claim 1, wherein the generated stimulation signal has a stimulation frequency in a range between 30 Hz and 10 Hz, 29 Hz and 11 Hz, 28 Hz and 12 Hz, 27 Hz and 13 Hz, 26 Hz and 14 Hz, 25 Hz and 15 Hz, 24 Hz and 16 Hz, 23 Hz and 17 Hz, 22 Hz and 18 Hz, or 21 Hz and 19 Hz.

8. The implantable device of claim 1, wherein the generated stimulation signal has a stimulation pulse width in a range of between 300 μs and 100 μs, 290 μs and 110 μs, 280 μs and 120 μs, 270 μs and 130 μs, 260 μs and 140 μs, 250 μs and 150 μs, 240 μs and 160 μs, 230 μs and 170 μs, 220 μs and 180 μs, or 210 μs and 190 μs.

9. The implantable device of claim 1, wherein the battery has a capacity in a range between 360 mAH and 100 mA, 350 mAH and 110 mAH, 340 mAH and 120 mAH, 330 mAH and 130 mAH, 320 mAH and 140 mAH, 310 mAH and 150 mAH, 300 mAH and 160 mAH, 290 mAH and 170 mAH, 280 mAH and 180 mAH, 270 mAH and 190 mAH, 260 mAH and 200 mAH, 250 mAH and 210 mAH, or 240 mAH and 220 mAH.

10. The implantable device of claim 1, wherein a total volume of the implantable device is in a range between 1.9 cc and 0.1 cc, 1.8 cc and 0.2 cc, 1.7 cc and 0.3 cc, 1.6 cc and 0.4 cc, 1.5 cc and 0.5 cc, 1.4 cc and 0.6 cc, 1.3 cc and 0.7 cc, 1.2 cc and 0.8 cc, or 1.1 cc and 0.9 cc.

11. The implantable device of claim 1, wherein the electrode assembly is separated from the enclosure by the lead by a distance in a range between 15 cm and 0.1 mm, 14 cm and 0.1 mm, 13 cm and 0.1 mm, 12 cm and 0.1 mm, 11 cm and 0.1 mm, 10 cm and 0.1 mm, 9 cm and 0.1 mm, 8 cm and 0.1 mm, 7 cm and 0.1 mm, 6 cm and 0.1 mm, 5 cm and 0.1 mm, 4 cm and 0.1 mm, 3 cm and 0.1 mm, 2 cm and 0.1 mm, or 1 cm and 0.1 mm.

12. The implantable device of claim 1, wherein the battery comprises a primary battery.

13. The implantable device of claim 12, wherein the primary battery comprises a rechargeable battery.

14. The implantable device of claim 1, wherein the enclosure comprises a fixation element to anchor into the nerve or other tissue, thereby reducing migration of the implantable device during long-term use in the subject.

15. The implantable device of claim 1, wherein at least a portion of the electrode assembly is configured for placement adjacent a nerve of the subject.

16. The implantable device of claim 1, wherein the electrode assembly comprises a fixation element, thereby reducing migration of the implantable device during long-term use in the subject.

17. The implantable device of claim 1, wherein the circuitry comprises a wireless communication transceiver configured to wirelessly communicate with an external programmer.

18. A system comprising:
the implantable device of claim 17; and
the external programmer, wherein the external programmer comprises a nerve stimulator.

19. The system of claim 18, wherein the nerve stimulator comprises one or more of a percutaneous tibial nerve stimulator or a transcatheter electrical nerve stimulator.

20. The implantable device of claim 17, wherein the wireless communication transceiver of the circuitry communicates with the external programmer through a conductive connection, and the wireless communication transceiver is configured to generate a communication signal received by the external programmer, the communication signal being one or more of below a threshold stimulation pulse amplitude, below a threshold stimulation pulse duration, or during a refractory period of a nerve.

21. The implantable device of claim 1, wherein the circuitry comprises a magnetic field sensor configured to detect a magnetic field.

22. The implantable device of claim 21, wherein the circuitry is configured to disable, postpone, or otherwise modify a therapeutic protocol of the implantable device in response to the detected magnetic field.

23. The implantable device of claim 22, wherein the detected magnetic field is generated from an external programmer to communicate with the circuitry of the implant.

24. The implantable device of claim 21, where in the magnetic field sensor comprises a giant magnetoresistance (GMR) switch.

25. The implantable device of claim 1, wherein the generated stimulation signal is configured to treat one or more of urinary incontinence, bowel incontinence, acute pain, chronic pain, hypertension, congestive heart failure, gastro-esophageal reflux, obesity, erectile dysfunction, insomnia, a movement disorder, or a psychological disorder.

26. The implantable device of claim 1, wherein the electrode assembly comprises one or more of a unipolar electrode, bipolar electrodes, or tripolar electrodes.

27. The implantable device of claim 1, wherein one or more of the lead or the electrode assembly comprises a connector removably coupling the electrode assembly to the lead or the enclosure.

28. The implantable device of claim 1, wherein the enclosure comprises an insulative outer coating.

29. The implantable device of claim 1, wherein the electrode assembly comprises a return electrode disposed on or integral with the enclosure.

30. The implantable device of claim 1, further comprising an accelerometer coupled to the circuitry, wherein the accelerometer is configured to detect an orientation or alignment of the implantable device or a movement of the subject.

31. The implantable device of claim 30, wherein the circuitry is configured to disable, postpone, or otherwise modify a therapeutic protocol of the implantable device in response to the detected orientation, alignment, or movement.

32. The implantable device of claim 1, wherein the electrode assembly is configured to direct the generated stimulation signal to one or more of a greater occipital nerve, a tibial nerve, a superficial peroneal nerve, a saphenous nerve, an intercostal nerve, a subcostal nerve, a lumbar plexus, a sacral plexus, a femoral nerve, a pudendal nerve, a sciatic nerve, a femoral nerve, a deep peroneal nerve, a common peroneal nerve, an ulnar nerve, an obturator nerve, a genitofemoral nerve, an iliohypogastric nerve, a median nerve, a radial nerve, a musculocutaneous nerve, a brachial plexus, or other peripheral nerve of the subject.

* * * * *